US007899225B2

(12) United States Patent
Collins et al.

(10) Patent No.: US 7,899,225 B2
(45) Date of Patent: Mar. 1, 2011

(54) SYSTEMS AND METHODS OF CLINICAL STATE PREDICTION UTILIZING MEDICAL IMAGE DATA

(75) Inventors: D. Louis Collins, St-Lambert (CA); Simon Duchesne, Montreal (CA)

(73) Assignee: McGill University, Montreal, Quebec (CA)

( * ) Notice: Subject to any disclaimer, the term of this patent is extended or adjusted under 35 U.S.C. 154(b) by 945 days.

(21) Appl. No.: 11/553,364

(22) Filed: Oct. 26, 2006

(65) Prior Publication Data

US 2008/0101665 A1    May 1, 2008

(51) Int. Cl.
  *G06K 9/00*  (2006.01)
  *A61B 5/05*  (2006.01)
  *A61B 8/00*  (2006.01)
  *A61B 5/00*  (2006.01)

(52) U.S. Cl. ......... 382/128; 600/300; 600/407; 600/425; 600/437

(58) Field of Classification Search .......... 382/128–132; 702/19; 600/300, 407, 425, 436, 437
See application file for complete search history.

(56) References Cited

U.S. PATENT DOCUMENTS

| 5,109,868 | A * | 5/1992 | Smith et al. ................... 600/587 |
| 5,724,379 | A * | 3/1998 | Perkins et al. ..................... 705/2 |
| 6,409,664 | B1 * | 6/2002 | Kattan et al. .................. 600/300 |
| 2004/0072143 | A1 * | 4/2004 | Timmis et al. .................... 435/4 |
| 2004/0147815 | A1 * | 7/2004 | Skinner .......................... 600/300 |
| 2005/0085709 | A1 * | 4/2005 | Pelletier et al. ............... 600/410 |
| 2005/0210015 | A1 * | 9/2005 | Zhou et al. ........................ 707/3 |
| 2006/0104494 | A1 | 5/2006 | Collins et al. |
| 2007/0106479 | A1 * | 5/2007 | Geerts et al. .................... 702/19 |
| 2007/0156344 | A1 * | 7/2007 | Sender et al. ................... 702/19 |

OTHER PUBLICATIONS

Scahill et al. ("Mapping the evolution of regional atrophy in Alzheimer's disease: Unbiased analysis of fluid-registered serial MRI", PNAS/Apr. 2, 2002/ vol. 99/ no. 7/ pp. 4703-4707).*
"High-dimensional pattern regression using machine learning: From medical images to continuous clinical variables"; Ying Wang, Yong Fan, Priyanka Bhatt, Christos Davatzikos; NeuroImage 50 (2010) 1519-1535; Section of Biomedical Image Analysis, Department of Radiology, University of Pennsylvania, Philadelphia, PA 19104, USA; Available online Jan. 4, 2010.
PubMed U.S. National Library of Medicine National Institutes of Health; Display Settings: Abstract; Neuroradiology. Jan. 2002 44(1):43-8; "Five-year retrospective changes in hippocampal atrophy and cognitive screening test performances in very mild Alzheimer's disease: the Tajiri Project" Yamaguchi S, Meguro K, Shimada M, Ishizaki J, Yamadori A, Sekita Y; Department of Disability Medicine, Tohoku University Graduate School of Medicine, Sendai, Japan.
Neurology India, Publication of the Neurological Society of India; Original Article Year : 2004 | vol. 52 | Issue : 3 | p. 332-337 "T2-weighted MRI in Parkinson's disease; Substantia nigra pars compacta hypointensity correlates with the clinical scores"; Huseyin Tugrul Atasoy, Oguz Nuyan, Tugba Tunc, Mehmet Yorubulut, Aysun E Unal, Levent E Inan Zonguldak Karaelmas University, Faculty of Medicine Neurology Department, Turkey.

(Continued)

*Primary Examiner* — Anand Bhatnagar
*Assistant Examiner* — Amara Abdi
(74) *Attorney, Agent, or Firm* — Anglehart et al.

(57) ABSTRACT

There is provided a method for predicting a clinical state of a subject based on image data obtained from a Volume Of Interest in the subject. The method comprise the establishment of a predictive model that relates image features and the future evolution of a clinical state.

32 Claims, 13 Drawing Sheets

OTHER PUBLICATIONS

"Voxel-Based Morphometry—The Methods"; John Ashburner and Karl J. Friston; NeuroImage 11, 805-821 (2000) doi:10.1006/nimg.2000.0582, available online at http://www.idealibrary.com; The Wellcome Department of Cognitive Neurology, Institute of Neurology, Queen Square, London WC1N 3BG, United Kingdom Received Oct. 22, 1999.

"Automated Image Registration: II. Intersubject Validation of Linear and Nonlinear Models"; Woods, Roger P.; Grafton, Scott T.; Watson, John D. G.; Sicotte, Nancy L.; Mazziotta, John C.Journal of Computer Assisted Tomography NumÃ© ro : vol. 22(1), Jan./Feb. 1998, pp. 153-165 CopyrightÃ : © Lippincott-Raven Publishers.

State of the Art; "Neuroimaging and Early Diagnosis of Alzheimer Disease: A Look to the Future1"; Jeffrey R. Petrella, MD; R. Edward Coleman, MD; P. Murali Doraiswamy, MD; Published online before print 10.1148/radiol.2262011600 Radiology 2003; 226:315-336; vol. 226 No. 2.

"Mesial temporal damage in temporal lobe epilepsy: a volumetric MRI study of the hippocampus, amygdala ans parahippocampal region"; N. Bernasconi, A. Bernasconi, Z. Caramanos, S.B. Antel, F. Andermann and D. L. Arnold; Department of Neurology and Neurosurgery, McGill University and Montreal Nurological Institute and Hospital, Montreal, Quebec, Canada; Brain (2003), 126, 462-469.

"Temporal Lobe Epilepsy Lateralization Based on MR Image Intensity and Registration Features" S. Duchesne, N. Bernasconi, A. Janke, A. Bernasconi, and D.L. Collins Montreal Neurological Institute, McGill Univ., Montreal, Canada 2 Center for Magnetic Resonance, Univ. of Queensland, Brisbane, Australia; R.E. Ellis and T.M. Peters (Eds.): MICCAI 2003, LNCS 2878, pp. 367-374, 2003; Springer-Verlag Berlin Heidelberg 2003.

"Active Appearance Models"; Timothy F. Cootes, Gareth J. Edwards, and Christopher J. Taylor; IEEE Transactions on Pattern Analysis and Machine Intelligence, vol. 23, No. 6, Jun. 2001.

2001 ISMRM Young Investigator Moore Award Papers; "4D Deformation Modeling of Cortical Disease Progression in Alzheimer's Dementia"; Andrew L. Janke, Greig de Zubicaray, Stephen E. Rose, Mark Griffin, Jonathan B. Chalk, and Graham J. Galloway; Magnetic Resonance in Medicine 46:661-666 (2001); 1Center for Magnetic Resonance, University of Queensland, Brisbane, Queensland, Australia. Department of Medicine, University of Queensland, Brisbane, Queensland, Australia. Grant sponsors: SmithKline Beecham Pharmaceuticals; Sylvia and.

"Automatic 3-D Model-Based Neuroanatomical Segmentation"; D.L. Collins, C.J. Holmes, T.M. Peters, and A.C. Evans; Human Brain Mapping 3:190-208(1995); McConnell Brain Imaging Centre, Montreal Neurological Institute, McGill University, Montreal, Canada.

"Automated Model-Based Tissue Classification of MR Images of the Brain"; Koen Van Leemput,* Frederik Maes, Dirk Vandermeulen, and Paul Suetens; IEEE Transactions on Medical Imaging, vol. 18, No. 10, Oct. 1999.

"A Nonparametric Method for Automatic Correction of Intensity Nonuniformity in MRI Data"; John G. Sled,* Alex P. Zijdenbos, Member, IEEE, and Alan C. Evans; IEEE Transactions on Medical Imaging, vol. 17, No. 1, Feb. 1998.

"Predictive Model for Assessing Cognitive Impairment by Quantitative Electroencephalography"; Joji Onishi, MD, Yusuke Suzuki, MD, PhD, Kenichi Yoshiko, MSc, Shin Hibino, PhD, and Akihisa Iguchi, MD, PhD; Cog Behav Neurol vol. 18, No. 3, Sep. 2005.

"Amygdalar volume and psychiatric symptoms in Alzheimer's disease: an MRI analysis"; Hor'i'nek D, Petrovicky' P, Hort J, Kra'sensky' J, Brabec J, Bojar M,Vane'c'kova' M, Seidl Z.; Acta Neurol Scand 2006: 113: 40-45.; Blackwell Munksgaard 2006.

"White matter damage of patients with Alzheimer's disease correlated with the decreased cognitive function"; Jin-Hai Duan, Hua-Qiao Wang, Jie Xu, Xian Lin; Shao-Qiong Chen, Zhuang Kang, Zhi-Bin Yao; Surg Radiol Anat (2006) 28: 150-156.

"Focal Decline of Cortical Thickness in Alzheimer's Disease Identified by Computational Neuroanatomy"; Jason P. Lerch, Jens C. Pruessner, Alex Zijdenbos, Harald Hampel, Stefan J. Teipel and Alan C. Evans McConnell Brain; Imaging Centre, Montreal Neurological Institute, McGill University, Montreal, Quebec, Canada, and Alzheimer Memorial Center, Dementia Research Section and Memory Clinic, Department of Psychiatry, Ludwig-Maximilian University, Munich, Germany; Cerebral Cortex Jul. 2005;15:995-1001; Cerebral Cortex V 15 N 7 Oxford University.

"Predicting conversion to dementia in mild cognitive impairment by volumetric and diffusivity measurements of the hippocampus"; Andreas Fellgiebela, Paulo R. Dellanib, Dirk Greverusa, Armin Scheuricha,Peter Stoeterb, Matthias J. Müllera; Department of Psychiatry, University of Mainz, Untere Zahlbacher Str. 8, D-55131 Mainz, Germany bInstitute of Neuroradiology, University of Mainz, Mainz, Germany; Psychiatry Research: Neuroimaging 146 (2006) 283-287.

"Conversion of Mild Cognitive Impairment to Alzheimer Disease Predicted by Hippocampal Atrophy Maps"; Liana G. Apostolova, MD; Rebecca A. Dutton, BS; Ivo D. Dinov, PhD; Kiralee M. Hayashi, BS; Arthur W. Toga, PhD; Jeffrey L. Cummings, MD; Paul M. Thompson, PhD; Arch Neurol/vol. 63, May 2006.

"Early DAT is distinguished from aging by high-dimensional mapping of the hippocampus"; J.G. Csernansky, MD; L. Wang, PhD; S. Joshi, PhD; J.P. Miller, AB; M. Gado, MD; D. Kido, MD;D. McKeel, MD; J.C. Morris, MD; and M.I. Miller, PhD; Neurology 55 Dec. (1 of 2) 2000.

"Morphological classification of brains via high-dimensional shape transformations and machine learning methods" Zhiqiang Lao, Dinggang Shen, Zhong Xue, Bilge Karacali, Susan M. Resnick, and Christos Davatzikos; Section for Biomedical Image Analysis, Department of Radiology, University of Pennsylvania, Philadelphia, PA 19104, USA; Laboratory of Personality and Cognition, National Institute on Aging, Baltimore, MD, USA; NeuroImage 21 (2004) 46-57.

"Discriminative MR Image Feature Analysis for Automatic Schizophrenia and Alzheimer's Disease Classification"; Yanxi Liu, Leonid Teverovskiy, Owen Carmichael, Ron Kikinis,Martha Shenton, Cameron S. Carter, V. Andrew Stenger, Simon Davis,Howard Aizenstein, James T. Becker, Oscar L. Lopez, and Carolyn C. Meltzer Carnegie Mellon University, Harvard Medical School, University of Pittsburgh; C. Barillot, D.R. Haynor, and P. Hellier (Eds.): MICCAI 2004, LNCS 3216, pp. 393-401, 2004; Springer-Verlag Berlin Heidelberg 2004.

IEEE Transactions on Medical Imaging, vol. 17, No. 3, Jun. 1998 475; "MR Image Texture Analysis Applied to the Diagnosis and Tracking of Alzheimer's Disease"; Peter A. Freeborough* and Nick C. Fox.

"A Unified Statistical Approach to Deformation-Based Morphometry"; M. K. Chung, K. J. Worsley, T. Paus,C. Cherif, D. L. Collins, J. N. Giedd, J. L. Rapoport, and A. C. Evans; Department of Mathematics and Statistics and Montreal Neurological Institute, McGill University, Montreal, Quebec, Canada; Departement de Mathematiques, Ecole Polytechnique Federale de Lausanne, Switzerland; and Child Psychiatry Branch, National Institute of Mental Health, NIH, Bethesda, Maryland 20892; NeuroImage 14, 595-606 (2001).

"Relating one-year cognitive change in mild cognitive impairment to baseline MRI features";Simon Duchesne, Anna Caroli, Cristina Geroldi, D. Louis Collins, Giovanni B. Frisoni; NeuroImage 47 (2009) 1363-1370.

* cited by examiner

| Groups | Decliners | Stable | Improvers |
|---|---|---|---|
| Subjects | 16 | 26 | 5 |
| Mean age (yrs) Std dev | 72.4 (4.7) | 67.6 (8.5) | 71.8 (5.4) |
| Baseline MMSE Std dev | 27.5 (1.3) | 27.8 (1.4) | 24.8 (1.8) |
| Mean MMSE Δ Std dev | -2.9 (1.2) | 0 (0.8) | 2.4 (0.6) |

SYSTEMS AND METHODS OF CLINICAL STATE PREDICTION UTILIZING MEDICAL IMAGE DATA

CROSS-REFERENCE TO RELATED APPLICATION

This is the first application filed for the present invention.

FIELD OF THE INVENTION

The present invention relates to computer-aided method and system predicting a clinical state of a subject via analysis of in vivo medical images.

BACKGROUND OF THE INVENTION

Medical imaging is widely used for diagnosis purposes and a general approach for diagnosis is to detect subtle differences in the composition, morphology or other behavior in organs as can be imaged by different techniques and equipment (ie. modalities) and relate these differences to clinical phenomena of interest.

Image data can be obtained from various sources including for example TI weighted Magnetic Resonance Imaging ("T1w MRI"), T2 weighted MRI ("T2w MRI"), Proton Density weighted MRI ("PD MRI"), Photon Emission Tomography ("PET"), Single Photon Emission Computer Tomography ("SPECT') and Computer Tomography ("CT").

Diagnosis of diseases based solely on their imaging characteristics is a challenging task for computer vision. If successful, however, diagnosis approaches can serve multiple purposes such as disease characterization or the morphological assessment of drug effect. Many studies have been conducted to find correlations between image and disease some examples are provided in the following references:

P. A. Freeborough and N. C. Fox, "MR image texture analysis applied to the diagnosis and tracking of Alzheimer's disease," IEEE Trans Med Imaging, vol. 17, pp. 475-9, 1998; J. P. Lerch, J. C. Pruessner, A. Zijdenbos, H. Hampel, S. J. Teipel, and A. C. Evans, "Focal decline of cortical thickness in Alzheimer's disease identified by computational neuroanatomy," Cereb Cortex, vol. 15, pp. 995-1001, 2005; Y. Liu, L. Teverovskiy, O. Carmichael, R. Kikinis, M. Shenton, C. S. Carter, V. A. Stenger, S. Davis, H. Aizenstein, J. T. Becker, O. L. Lopez, and C. C. Meltzer, "Discriminative MR Image Feature Analysis for Automatic Schizophrenia and Alzheimer Disease Classification," presented at Medical Image Computing and Computer Assisted Intervention, Saint-Malo, France, 2004; Z. Lao, D. Shen, Z. Xue, B. Karacali, S. M. Resnick, and C. Davatzikos, "Morphological classification of brains via high-dimensional shape transformations and machine learning methods," Neuroimage, vol. 21, pp. 46-57, 2004; J. G. Csernansky, L. Wang, S. Joshi, J. P. Miller, M. Gado, D. Kido, D. McKeel, J. C. Morris, and M. I. Miller, "Early DAT is distinguished from aging by high-dimensional mapping of the hippocampus. Dementia of the Alzheimer type," Neurology, vol. 55, pp. 1636-43, 2000; L. G. Apostolova, R. A. Dutton, I. D. Dinov, K. M. Hayashi, A. W. Toga, J. L. Cummings, and P. M. Thompson, "Conversion of mild cognitive impairment to Alzheimer disease predicted by hippocampal atrophy maps," Arch Neurol, vol. 63, pp. 693-9, 2006; P. Golland, W. E. Grimson, M. E. Shenton, and R. Kikinis, "Detection and analysis of statistical differences in anatomical shape," Med Image Anal, vol. 9, pp. 69-86, 2005; Psychiatry Res. Apr. 30, 2006;146(3):283-7. Epub Mar. 10, 2006. Predicting conversion to dementia in mild cognitive impairment by volumetric and diffusivity measurements of the hippocampus. Fellgiebel A, Dellani P R, Greverus D, Scheurich A, Stoeter P, Muller M J. Surg Radiol Anat. 2006 May; 28(2):150-6. White matter damage of patients with Alzheimer's disease correlated with the decreased cognitive function. Duan J H, Wang H Q, Xu J, Lin X, Chen S Q, Kang Z, Yao Z B. Acta Neurol Scand. 2006 January; 113(1):40-5. Amygdalar volume and psychiatric symptoms in Alzheimer's disease: an MRI analysis. Horinek D, Petrovicky P, Hort J, Krasensky J, Brabec J, Bojar M, Vaneckova M, Seidl Z.Neurol India. 2004 September; 52(3): 332-7. T2-weighted MRI in Parkinson's disease; substantia nigra pars compacta hypointensity correlates with the clinical scores. Atasoy H T, Nuyan Q, Tunc T, Yorubulut M, Unal A E, Inan L E. Neuroradiology. 2002 January; 44(1):43-8. Five-year retrospective changes in hippocampal atrophy and cognitive screening test performances in very mild Alzheimer's disease: the Tajiri Project. Yamaguchi S, Meguro K, Shimada M, Ishizaki J, Yamadori A, Sekita Y. Neuroreport. Dec. 3, 2003; 13(17):2299-302. Diffusion tensor in posterior cingulate gyrus: correlation with cognitive decline in Alzheimer's disease. Yoshiura T, Mihara F, Ogomori K, Tanaka A, Kaneko K, Masuda K. Arch Gerontol Geriatr. May 22, 2006; Linear measures of temporal lobe atrophy on brain magnetic resonance imaging (MRI) but not visual rating of white matter changes can help discrimination of mild cognitive impairment (MCI) and Alzheimer's disease (AD). Saka E, Dogan E A, Topcuoglu M A, Senol U, Balkan S. Psychiatry Clin Neurosci. 2006 June; 60(3):319-26. Association of minimal thickness of the medial temporal lobe with hippocampal volume, maximal and minimal hippocampal length: volumetric approach with horizontal magnetic resonance imaging scans for evaluation of a diagnostic marker for neuroimaging of Alzheimer's disease. Uotani C, Sugimori K, Kobayashi K. Cogn Behav Neurol. 2005 September; 18(3):179-84. Predictive model for assessing cognitive impairment by quantitative electroencephalography. Onishi J, Suzuk Y, Yoshiko K, Hibino S, Iguch A.

However, diagnosis approaches, while providing important information on the state of an individual at a point in time, does not in itself provides an assessment of the future evolution of a particular clinical state. Such predictions are only based on the experience of medical practitioners and are a very subjective estimation of the future evolution of a clinical state.

SUMMARY OF THE INVENTION

In a broad aspect of the invention, there is provided a method for predicting the future evolution of a clinical state of a subject based on analysis of imaging data. The method advantageously provides an objective approach to the prediction of future clinical state.

In one embodiment, the method comprises providing a statistical image-based predictive model for predicting the evolution of the state, the model incorporating one or more image-derived features from at least one volume of interest (VOI) comprising information related to the clinical state, collecting image data from the at least one VOI in the subject, deriving the one or more image features from the collected image data from the subject, and using the one or more derived image features from the at least one VOI of the subject and the predictive model to predict the evolution of the clinical state.

In another embodiment of the invention the predictive model can be obtained by deriving a set of modes of variation of the image features from a plurality of training subjects, selecting a subset of the modes of variation based on a first univariate or multivariate analysis or combination thereof between the modes of variation and at least one clinical variable, and establishing the model based on a second univariate, or multivariate analysis or combination thereof between the selected subset of modes and the at least one clinical variable.

BRIEF DESCRIPTION OF THE DRAWINGS

In drawings which illustrate by way of example only embodiments of the present invention:

FIG. 1 is a schematic illustration of the design of an automated classification system;

FIG. 2 is a flow chart, illustrating exemplary steps performed at a computing device of FIG. 1;

FIG. 3 is a flow chart, further illustrating the data collection step of FIG. 2;

FIG. 4 is a flow chart, further illustrating the VOI selection step of FIG. 2;

FIG. 5 is a flow chart, further illustrating the intensity data calculation step of FIG. 2;

FIG. 6 is a flow chart, further illustrating the spatial data calculation step of FIG. 2;

FIG. 7 is a flow chart, further illustrating the variation model creation step of FIG. 2;

FIG. 8 is a flow chart, further illustrating the classifier building step of FIG. 2;

FIG. 9 is a flow chart, further illustrating the test patient classification step of FIG. 2;

DETAILED DESCRIPTION

For explanatory purposes FIG. 1 through 9 will be generally discussed prior to the detailed description of the invention.

Figure 1:
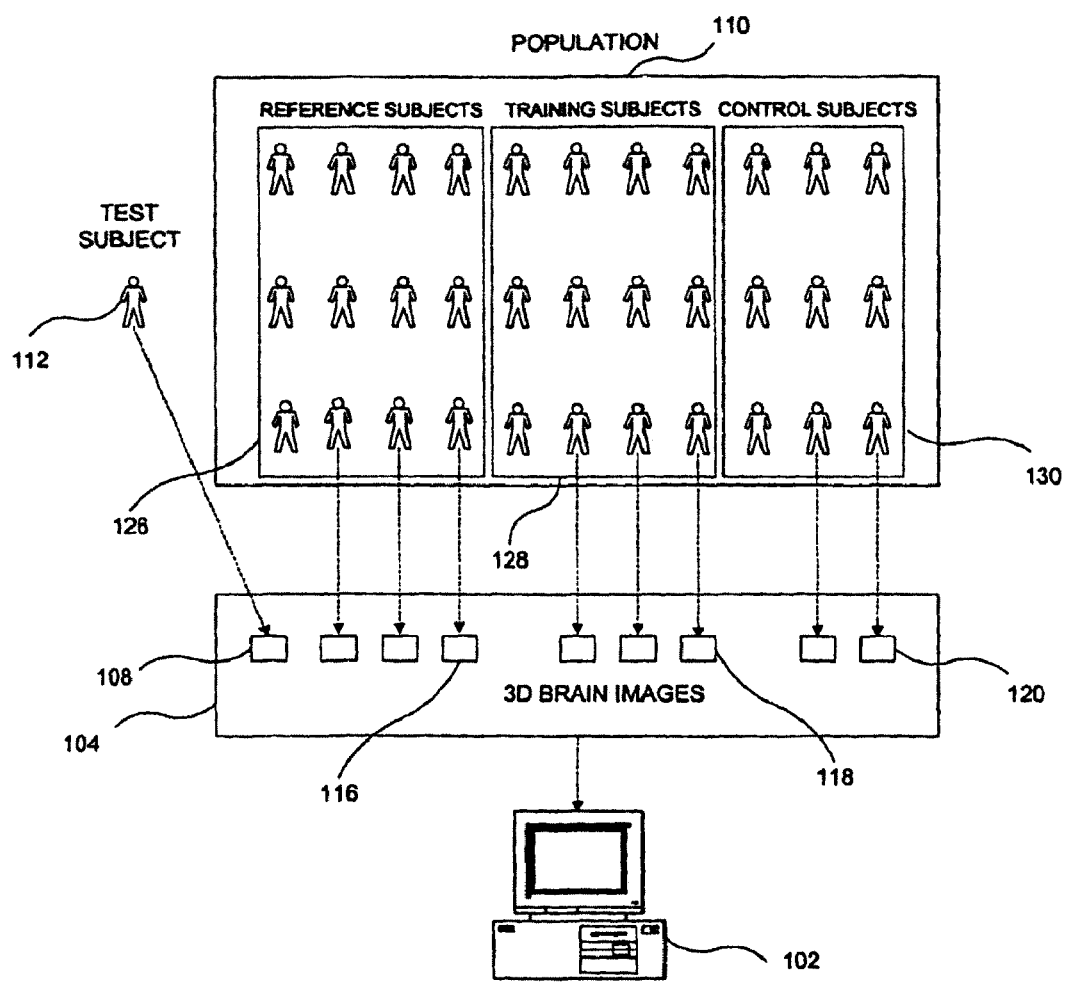
FIGS. 1 to 9 are representative of the prior art.

A schematic illustration of the design of an automated classification system 102 in manners exemplary of the present invention is shown in FIG. 1. The example automated classification system 102 determines a classification and diagnosis of the neurological disease state of a given test subject 112, based on 3D image data of the brain 104. The image data 104 may be mono-modal or multi-modal. Possible types of images that may be acquired include, but are not limited to images based on: T1w MRI, T2w MRI, PD MRI, PET, SPECT, and CT.

As illustrated, example automated classification system 102 is determined using a general purpose computing device, executing software exemplary of the aspects of the present invention. The computing device may have any suitable combination of dynamic and persistent storage memory. To classify the disease state of a test subject 112, a plurality of 3D images 104 is first collected from subjects in population 110 (in some embodiments, typically only one image is collected for each subject). The subjects within population 110 consist of three separate groups: reference subjects 126, training subjects 128, and control subjects 130. This results in a set of reference subject images 116, training subject images 118, and control subject images 120. In a preferred embodiment, all subject images are acquired using the same standard, one example for which is described in Mazziofta J C, Toga A W, Evans A, Fox P, Lancaster J, "A probabilistic atlas of the human brain: theory and rationale for its development", The International Consortium for Brain Mapping (ICBM), Neuroimage 1995, 2(2):89-101, the contents of which are incorporated herein by reference.

This image data is presented to the classification system 102 to train itself in the classification of a particular neurological disease or disorder. The automated classification system 102, once trained, may then classify any test subject 112 on the basis of that subject's image data 108.

Figure 2:
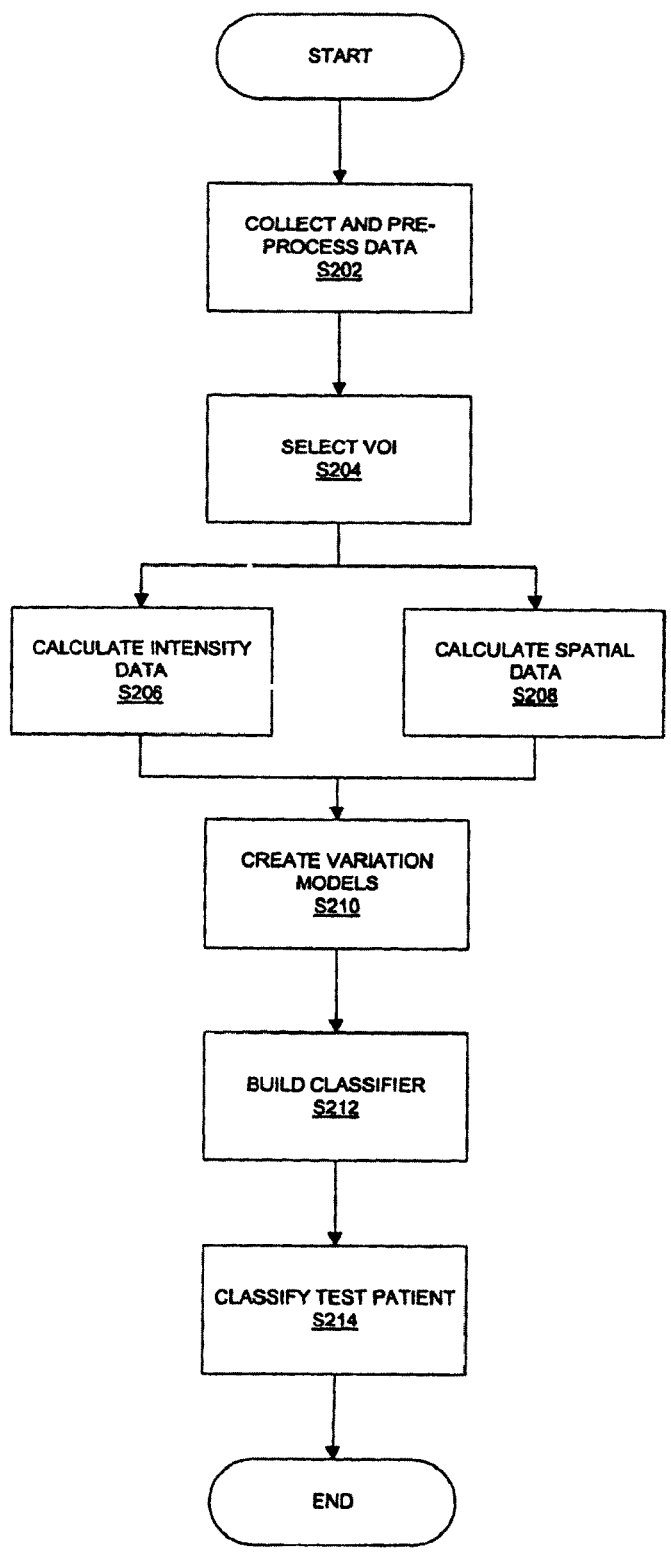

The exemplary steps performed by the automated classification system 102 are illustrated in the flow chart shown in FIG. 2. In step S202, 3D image data 104 is first collected from the scanner and pre-processed. Following image acquisition, known types of preprocessing operations are typically executed to prepare the images for use in analysis in later steps. These preprocessing operations may include the correction of intensity inhomogeneities or global re-alignment (registration) of the image into a standard reference space. Based on standard reference coordinates, one or more particular volumes of interest (VOIs) within the brain are manually selected in step S204, the specific selection of a VOI depending on the particular disease that is to be classified. Both intensity and spatial characteristics of the image data are calculated in steps S206 and S208. These steps define the features of the images that will be analyzed in later steps. Statistical models are created in step S210 based on training subject images 118 and define multi-dimensional spaces within which subjects may be represented. These statistical models are merged to create one single, final multi-dimensional classification space or universe. In step S212, a classifier is built within this classification space based on control group image data 120 and divides the universe of subjects into two or more regions, such that each region defines a space of subjects having a particular condition (or state of nature). This classifier is then used in step S214 to identify and characterize the disease state of individuals, such as a test patient 112, based on the location of an individual's representation within the classification space.

Figure 3:
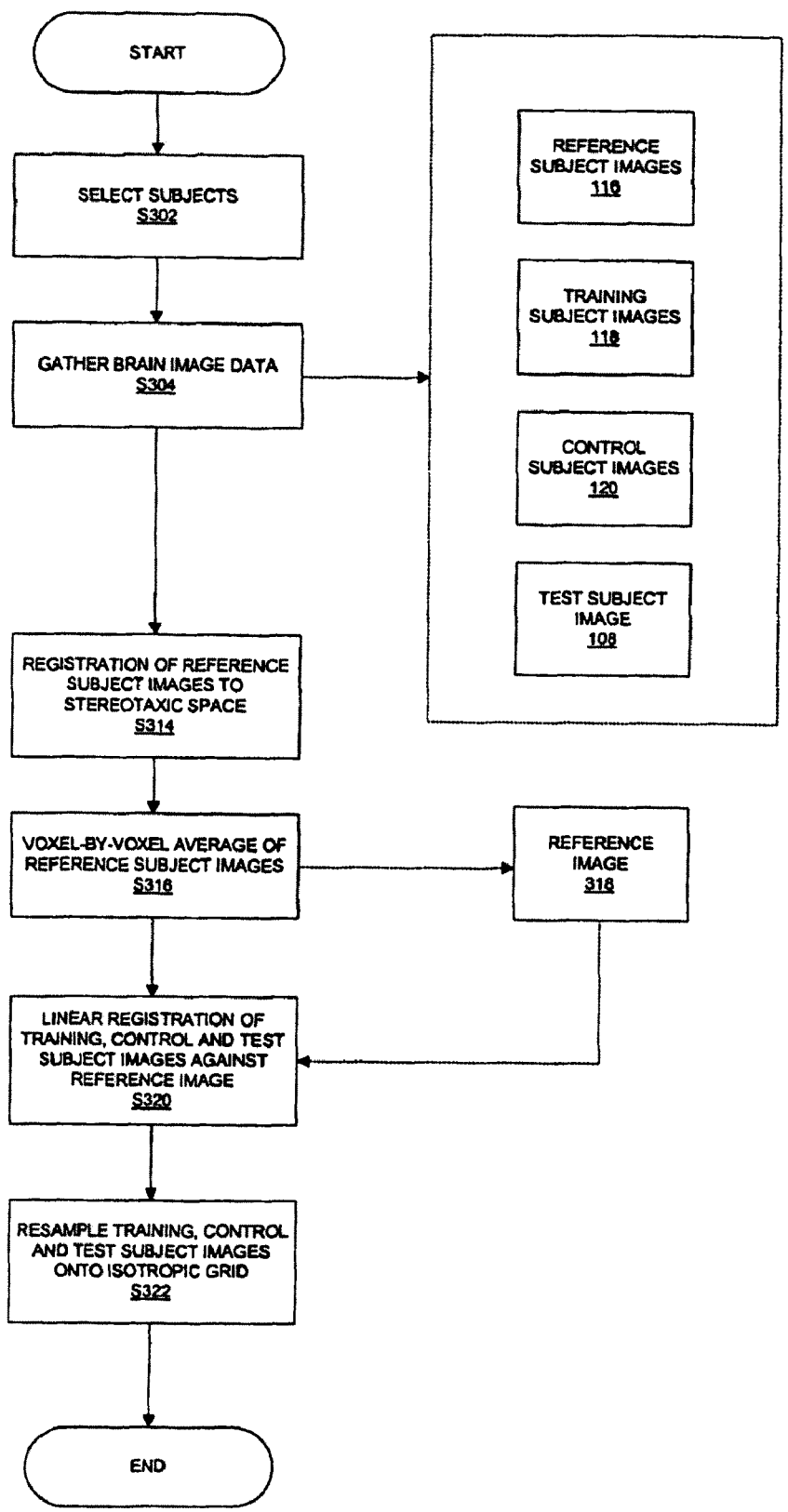

The data collection step S202 is more particularly illustrated in FIG. 1 and FIG. 3. Prior to the processing of any data by the automated classification system 102, subjects are selected in step S302. For each selected subject, brain image data is acquired in step S304 using an appropriate medical imaging device. This results in image data 116, 118, 120 for reference subjects, training subjects, and control subjects, respectively. This is the image data that is required in order to build and train the automated classification system 102 to diagnose and classify a particular neurological disease or disorder. Test subject image data 108 is also obtained for the individuals whose neurological disease state is to be diagnosed and classified by the automated classification system 102. Possible types of images that may be acquired include, but are not limited to: T1w MRI, T2w MRI, PD MRI, PET, SPECT, and CT. The nature of the information encoded at each voxel of the image data will depend on the particular imaging modality chosen, and thus the term "intensity" and "image signal" are intended to cover the different possibilities corresponding to the different modalities.

The subjects may be chosen in step S302 in a number of different ways, understood by a person skilled in the art, in order to discriminate between groups of subjects on the hypothesis that there exists intensity and spatial differences between brain images of individuals in the groups. Groups of subjects need not always include "normal" non-pathological individuals. For example, the classifier may be used to separate between groups of pathological individuals. In order to capture the variability between individual subjects within the statistical models, a large enough number of training subjects 128, must be selected. Selecting a minimum of 30-40 training subjects 128 is sufficient. Similarly, the selection of a minimum of 30-40 control subjects 130 is sufficient for determining functions that divide the universe of subjects into classification regions. It is not necessary that the group of control subjects contain known members of each possible condition (or state of nature). For example, pathological individuals of a particular condition (or state of nature) might be classified by the system on the basis of a control group consisting solely of known pathological subjects of that particular condition (in such an embodiment, a different model for the definition of membership within each classification region would be built than one for which the control group contains known member of each possible condition). In a preferred embodiment, the training subject images 118 and the control subject images 120 are obtained from two distinct groups of subjects in order to ensure statistical independence.

Global intensity correction is typically performed on all of the images in order to correct intensity inhomogeneities due to scanner variations (not shown in FIG. 3.) A number of standard techniques may be used to accomplish this. Two such techniques are described in J. G. Sled, A. P. Zijdenbos, and A. C. Evans, "A Nonparametric Method for Automatic Correction of Intensity Nonuniformity in MRI Data", IEEE Transactions on Medical Imaging, Vol. 17, No. 1, February 1998, pp. 87-97, and Van Leemput K, Maes F, Vandermeulen O, Suetens P, "Automated model-based bias field correction of MR images of the brain", IEEE Trans Med Imaging 1999, 18(10):885-96 the contents of which are hereby incorporated by reference.

As illustrated in FIG. 3, after subject selection S302 and brain image acquisition S304 there are different sets of subject images, 116, 118, 120, and 108. Each set of subject images serves a different purpose in the automated classification system 102. The present system does not require that all of these images be pre-processed in step S202 as shown in FIG. 3 at the same time (e.g. the test subject images 108 may be pre-processed at a separate time, possibly at a clinic for diagnosis).

Reference subject images 116 facilitate the comparison of the image data between different individuals by being the basis for the formation of a single reference image 318 against which all other images may be registered. After the reference image 318 is formed, the reference subject images 116 are no longer needed. The linear registration of an image against a reference image 318 in step S320 will globally align the image into a standard reference space, such as the Talairach space (a normalized coordinate system commonly used in the field of neuroscience). For example, the linear registration technique described in D. L. Collins, P. Neelin, T. M. Peters, and A. C. Evans, "Automatic 3D Intersubject Registration of MR Volumetric Data in Standardized Talairach Space", Journal of Computer Assisted Tomography, Vol 18(2), March/April 1994, pp. 192-205, the contents of which are hereby incorporated by reference, describes a method based on a 3D cross-correlation with an average brain image volume. An image may be quantitatively determined to be aligned into a standard reference space through the minimization of an error or cost function based on the cross-correlation of image gradients. Thus, reference subject images 116 are first each registered with a standard reference space in step S314. A voxel-by-voxel average of all of the reference subject images is then taken in step S316 to create a final, single reference image 318.

Training subject images 118 are used to build the statistical model, which are the mathematical variation models which define multi-dimensional spaces within which subjects may be represented. Control subject images 120 are used to build mathematical functions that will identify and characterize the disease state of individuals. Test subject images 108 are used to represent a test patient 112 who is to be classified by the classification system 102. All of these subject images are linearly registered in step S320 against the reference image 318. For example, a 9-degrees of freedom (3 translational, 3 rotational, 3 scaling) linear transformation that maximizes the cross-correlation between characteristics of a subject image and the reference image 318 at each voxel might be employed to accomplish the linear registration in step S320. Other linear transformation techniques can be employed in other embodiments. Initial processing of the subject images also includes resampling the data onto an isotropic grid in step S322. In a preferred embodiment, an isotropic grid with a resolution of 1 $mm^3$ is used. Other known pre-processing techniques that can be employed include AIR and SPM, described in Woods R P, Grafton S T, Watson J D, Sicotte N L, Mazziofta J C, "Automated image registration: II. Intersubject validation of linear and nonlinear models", Journal of Computer Assisted Tomography 1998, 22(1):153-165 and described in Ashburner J, Friston K J, "Voxel-based morphometry—the methods", Neuroimage 2000, 11(6 Pt 1):805-2100, respectively, the contents of each being incorporated herein by reference.

After image data has been collected and pre-processed in step S202 a large, non-specific volume of interest (VOI) is selected in step S204. This will typically be done manually by a person with sufficient experience to decide what is a suitable VOI in the particular circumstances. It is, however, contemplated to widen the search space so that even large (more than ⅓) portions of the brain might be sufficient to perform this task, regardless of anatomical variability. It is also contemplated that a computer with artificial intelligence might be programmed to perform this task.

Figure 4:
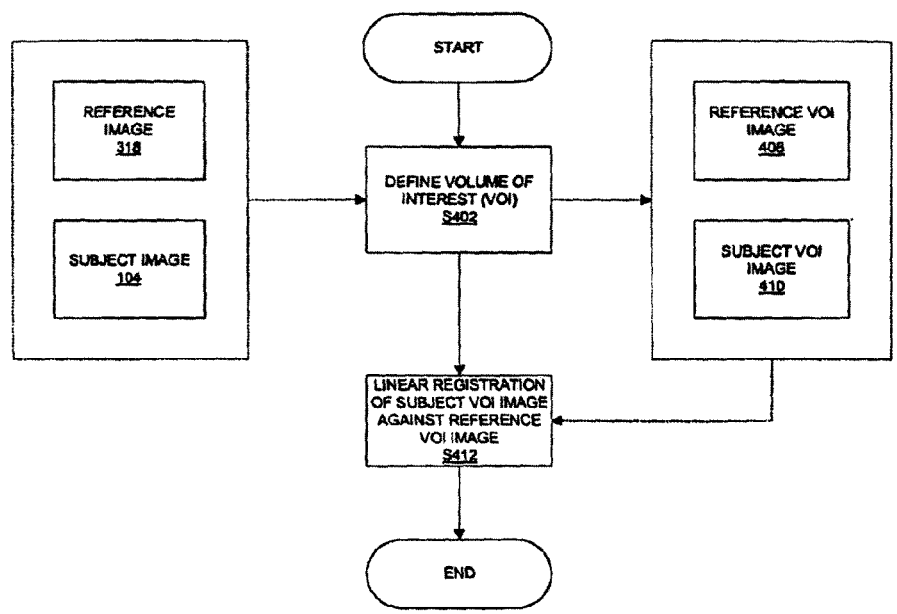

This step of selecting a VOI is more particularly illustrated in FIG. 4. The present system does not require that this step be performed for all of the subject images 104 at the same time (e.g. the test subject images 108 may be processed at a separate time, possibly at a clinic for diagnosis). The VOI is defined in step S402 for the purpose of extracting a specific portion of a global brain image for analysis. There are a number of advantages to using a relatively large, non-specific VOI. First, the VOI is useful because particular diseases will affect certain areas of the brain more than others. The VOI allows a focused analysis that reduces the noise introduced into the global analyses by parts of the brain outside of the VOI. However, it is not generally the case that only a single anatomical structure of the brain is affected by a given disease. Often there are complex interactions between brain components, which cannot be captured through the analysis of a single brain structure. Thus, the selection of a larger VOI in step S402 that encapsulates more than one brain structure enables the present invention to analyze characteristics of a specific volume in the brain without restricting analysis to a single brain structure.

The VOI will typically be selected to cover a larger region of interest than one specific brain component. Thus the VOI can be selected to encompass one or more specific components of the brain which are known to be associated with a specific pathology, and will provide a boundary that extends a distance beyond the edge of the component(s) of interest.

The VOI is also "non-specific" in the sense that absolute accuracy in the delineation of the boundary of the VOI is not essential. Even if the selection of a given VOI in step S402 is inaccurate (e.g. centimeters off from an optimal selection) the classification system will still likely function properly to classify a test subject. The larger the number of subjects used in training and building the system, the less precise the selection of the VOI needs to be. One practical advantage is that the selection of the VOI in step S402 may possibly be done by an individual who merely has neuroanatomical knowledge and does not necessarily need to be an individual with special expert medical or neuroscientific knowledge.

The present invention also combines the analysis of different features of both intensity and spatial shape characteristics of images. This allows even greater flexibility in the image analysis, since a different VOI may be selected at step S402 for each particular feature of interest that is to be analyzed. For example, one VOI may be selected for the analysis of a feature based on intensity data, while a second VOI may be selected for the analysis of a feature based on spatial data. The classification system will perform its analysis taking into account both VOIs. Thus, multiple and different VOIs may be defined for any given application of the classification system.

Once a VOI has been defined in step S402, that portion of the image is extracted from the global volume based on its standard reference (e.g. Talairach) coordinates. This extraction is performed for a given subject image 104 as well as the reference image 318, resulting in a reference VOI image 408 and a subject VOI image 410. To further reduce any positional variations in brain structures due to normal inter- and intra-individual variability not eliminated during the linear registration step S320 (since that step is a global registration of the entire image and not just the selected VOI), the subject VOI image 410 is linearly registered against the reference VOI image 408. For example, a 12-degrees of freedom (3 translational, 3 rotational, 3 scaling, 3 skewing) linear transformation that maximizes the cross-correlation between characteristics of a subject VOI 410 and the reference VOI 408 at each voxel might be employed to accomplish the linear registration. Some other possibilities for this linear registration of the subject VOI image against the VOI image include using fewer degrees of freedom, however a 12-degrees of freedom transform substantially reduces the "barrel effect", due to gradient coil inhomogeneity.

Figure 5:
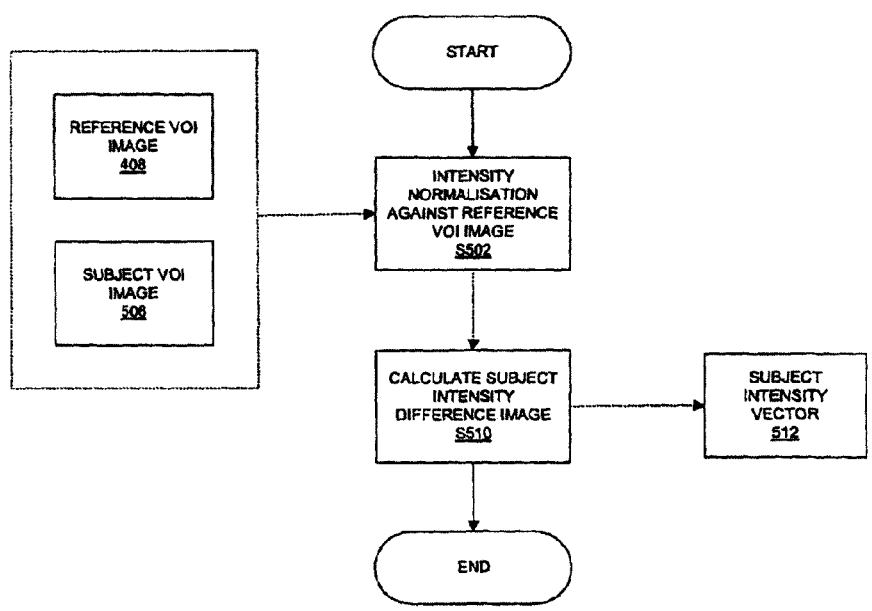

In step S206, training subject images 118, control subject images 120, and test subject images 108, are intensity processed as illustrated in FIG. 5. The present system does not require that all of these images be processed at the same time (e.g. the test subject images 108 may be processed at a separate time, possibly at a clinic for diagnosis). Intensity data for a given subject VOI image 506 is first intensity normalized in step S502 with respect to the reference VOI image 408 to reduce unwanted noise from the analysis. This produces a normalized subject VOI image. In intensity modeling, non-linear registration of the VOI is not performed because it would induce conformity in all data sets, potentially eliminating the pathological effects that are being modeled at the same time as the normal, anatomical variability.

Training subject normalized images 118, control subject normalized images 120, and test subject normalized images 108 are rasterized in step S510 to produce a subject intensity vector (i.e. single vector created by "unwrapping" the 3D image data). Subject intensity vector (g) 512 represents a particular feature of the VOI of a given subject. For example, the feature may be the voxel-by-voxel difference between a subject VOI image 506 and the mean of all subject VOI images 506 in the training group. The resulting subject intensity vector 512 would be:

$$g = v_{subject} - v_{average}$$

Other intensity based features might be determined through the use of texture operators to calculate voxel-wise higher-order intensity features.

Figure 6:
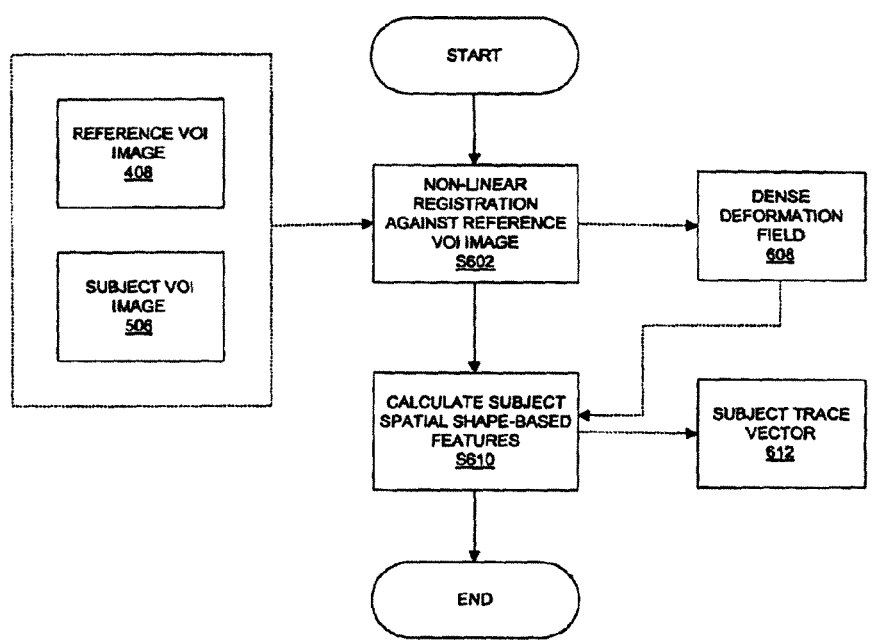

Spatial data is calculated for each subject VOI as well. In step S208, training subject images 118, control subject images 120, and test subject images 108, are processed for spatial shape-based features, as illustrated in FIG. 6. The present system does not require that all of these images be processed at the same time (e.g. the test subject images 108 may be processed at a separate time, possibly at a clinic for diagnosis). A non-linear registration of a given subject VOI image 506 against the reference VOI image 408 is performed first in step S602. Non-linear registration S602 attempts to match image features from a source volume to those of the reference image at a local level. The result of the non-linear registration is a dense deformation field 608 that captures the displacements required to align the subject VOI image 506 to the reference VOI image 408. A number of non-linear registration processes exist for performing this process. One example is ANIMAL, described in D. L. Collins, C. J. Holmes, T. M. Peters, and A. C. Evans, "Automatic 3-D Model-Based Neuroanatomical Segmentation", Human Brain Mapping, Vol. 3, 1995, pp. 190-208, the contents of which are hereby incorporated by reference. The ANIMAL algorithm attempts to match image grey-level intensity features at a local level in successive blurring steps, by minimizing the cross-correlation function of voxel intensities between source and reference images. For example, the non-linear transformation (represented by a deformation field 608) may first be determined at a low resolution (highly blurred data) with 8 mm of spacing between the nodes. The results are refined recursively by increasing the resolution to 4 mm, then 2 mm, and finally 1 mm. Another possible approach to non-linear registration may be to register the VOI using basis functions, and then perform an analysis of the basis function weights.

A series of calculations are performed in step S610 on the resulting dense deformation field 608 to produce a rasterized vector which represents a particular feature of the VOI of a given subject such as local volume change. Other examples might include torque or shift magnitude. A method of computing the local volume change at each voxel by using the rate of the Jacobian change of the deformation is described by M. K. Chung, K. J. Worsely, T. Paus, C. Cherif, D. L. Collins, J. N. Giedd, J. L. Rapoport, and A. C. Evans, "A Unified Statistical Approach to Deformation-Based Morphometry", NeuroImage, Vol. 14(3), 2001, pp. 595-606, the contents of which are hereby incorporated by reference. If U represents the deformation field which matches homologous points between two images by storing a 3-D displacement vector for each voxel, then the deformation in the Lagrangian coordinate system at time t is:

$$x \rightarrow x + U(x,t)$$

The local volume change of the deformation in the neighbourhood of any given voxel at a point x is determined by the Jacobian determinant J which is defined as:

$$J(x,t) = det\left(I + \frac{\partial U}{\partial x}\right)$$

where I denotes the identity matrix and 3×3 displacement gradient matrix ∇U is:

$$\nabla U = \frac{\partial U}{\partial x}(x,t) = \begin{pmatrix} \frac{\partial U_1}{\partial x_1} & \frac{\partial U_1}{\partial x_2} & \frac{\partial U_1}{\partial x_3} \\ \frac{\partial U_2}{\partial x_1} & \frac{\partial U_2}{\partial x_2} & \frac{\partial U_2}{\partial x_3} \\ \frac{\partial U_3}{\partial x_1} & \frac{\partial U_3}{\partial x_2} & \frac{\partial U_3}{\partial x_3} \end{pmatrix}$$

For relatively small displacements, the trace of the 3×3 displacement gradient ∇U is a crude yet indicative measure of local volume change:

$$J \approx 1 + tr(\nabla U)$$

Thus, a rasterized subject trace vector (t) 612, calculated at step S610, is an indicator of morphological change and represents a particular feature of the VOI of a given subject 506 (namely, the local volume change at each voxel). If the feature is the voxel-by-voxel difference between a subject VOI image 506 and the mean of all subject VOI images 506 in the training group, the resulting subject trace vector 612 would be:

$$t = v_{subject} - v_{average}$$

where, $$v = v_{local\ volume\ change} \approx tr(\nabla U)$$

One possible implementation of the trace calculation is discussed in A. L. Janke, G. de Zubicaray, S. E. Rose, M. Griffin, J. B. Chalk, and G. J. Galloway, "4D Deformation Modeling of Cortical Disease Progression in Alzheimer's Dementia", Magnetic Resonance in Medicine, Vol. 46, 2001, pp. 661-666, the contents of which are hereby incorporated by reference.

Another possibility for spatial modeling may be to use each of the differential elements in the displacement gradient matrix ∇U for tensor-based morphometry as described in Thompson P M, Giedd J N, Woods R P, MacDonald D, Evans A C, Toga A W, "Growth patterns in the developing brain detected by using continuum mechanical tensor maps", Nature 2000, 404(6774): 190-3, the contents of which are incorporated herein by reference.

Figure 7:
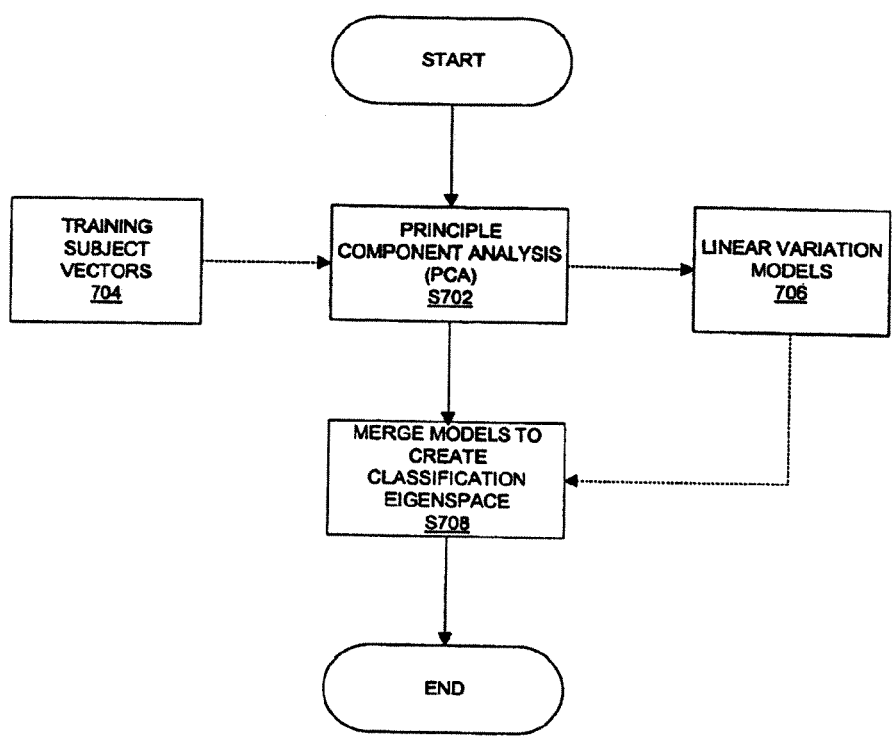

The creation of variation models in step S210 is more particularly illustrated in FIG. 7. In step S702 training subject vectors 704 are analyzed using Principal Components Analysis (PCA). In the intensity data and spatial data calculation steps S206, S208 discussed previously, a set of vectors are created that represent particular features of the VOI of a given training subject. For example, for each training subject there may exist a training subject trace vector (t) 612 and a training subject intensity vector (g) 512. Linear variation models 706 are created for each particular feature (e.g. one for local volume change and one for intensity difference).

For a given feature, if there are N subjects in the entire set of training subjects, and there are L number of voxels in the VOI, then each subject is a point in L-dimensional space. For example, each training subject trace vector (t) 612 is a vector of length L and the entire model training subject dataset 704 for the trace feature may be expressed in matrix form:

$$\begin{matrix} t_{1,1} & \cdots & t_{1,L} \\ M & O & \\ t_{N,1} & & t_{N,L} \end{matrix}$$

Application of PCA in step S702 to the model training subject dataset 704 results in a set of eigenvectors that characterize the training data. After this stage, the training subject data is no longer needed, as the statistical model has now been generated. As long as N<<L, then the total number of non-zero eigenvectors of the covariance matrix is N-I. These resulting eigenvectors may then be used to create a statistical model of the appearance of the image. For example, a linear variation model 706 can be generated that can describe any instance of a subject trace vector based on the training subject dataset 704. For example, using the notation identical to that in employed in T. F. Cootes, G. J. Edwards, and C. J. Taylor, "Active Appearance Models", IEEE Transactions on Pattern Analysis and Machine Intelligence, Vol. 23, No. 6, June 2001, pp. 681-685 (the contents of which are hereby incorporated by reference):

$$t = t_{mean} + P_t b_t$$

where $t_{mean}$ is the mean normalised trace vector, $P_t$ is the set of orthogonal modes of variation (eigenvectors) for the trace data and $b_t$ is a vector of parameters. A given subject trace vector is described by varying $b_t$. The upper bound on the dimensionality of $P_t$ and $b_t$ is the total number of eigenvectors, which is N-I.

Similarly, a linear variation model 706 may also be generated for the training intensity data:

$$g = g_{mean} + P_g b_g$$

A linear variation model 706 is generated for each set of training subject vectors 704 that represent a particular feature of the VOI. Generalized forms of the model training subject matrix 704 and linear variation model 706 are shown below.

$$\begin{matrix} x_{1,1} & \cdots & x_{1,L} \\ M & O & \\ x_{N,1} & & x_{N,L} \end{matrix}$$

$$x = x_{mean} + P_x b_x$$

where $$x_{mean} = \frac{1}{N}\sum_{i=1}^{N} x_i$$

$P_x$ is the set of orthogonal modes of variation; and
$b_x$ is a vector of parameters The ensemble of principal components from each of the linear variation models 706 define an Allowable Domain as the space of all possible elements expressed by the eigenvectors. For example, an Allowable Grey Domain G is defined by the intensity eigenvectors and an Allowable Trace Domain T is defined by the trace eigenvectors. We now wish to reduce the dimensionality of these Allowable Domains from the upper-bound of N-1. For example, in order to determine how each principle component contributes to the total variance of the system, the ratio of relative importance of the eigenvalue $\lambda_k$ associated with the eigenvector k might be used:

$$r_k = \frac{\lambda_k}{\sum_{j=1}^{N-1} \lambda_j}$$

where the fraction $r_k$ is the relative importance for eigenvalue $\lambda_k$. This information may be employed to reduce the dimensionality of the Allowable Domains by retaining fewer than N-1 eigenvectors, thus defining a restricted space Allowable Grey Domain G* and a restricted Allowable Trace Domain T*. It is contemplated that other types of linear variation models might also be created using other analytical methods, such as independent component analysis.

In step S708, the restricted spaces are merged to create a single, final classification eigenspace or universe C*. It is within this eigenspace that subjects are classified, based on their expressed eigencoordinates. For example, classification eigenspace C* may be created by merging restricted Allowable Trace Domain T* and restricted Allowable Grey Domain G*. Individuals can thus be represented in the space:

$$C^* = T^* \cup G^*$$

Figure 8:
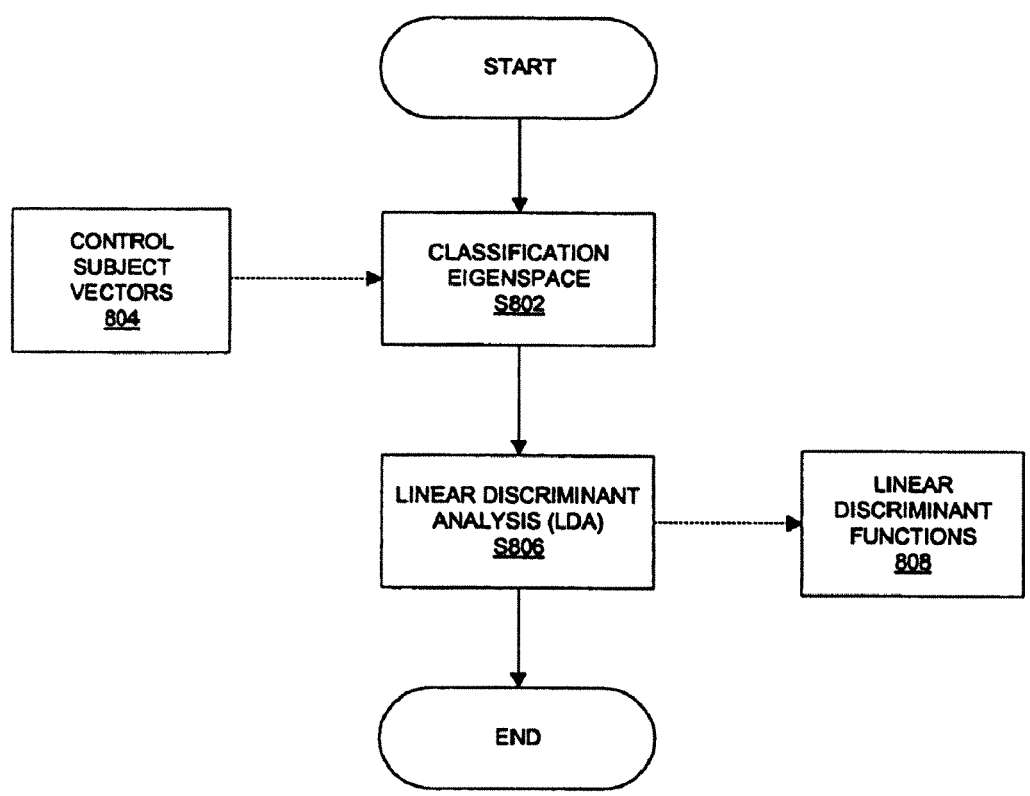

The classifier building step S212 is more particularly illustrated in FIG. 8. In this step, control subject vectors 804 are used to create discriminant functions 808 that divide the eigenspace into regions to classify a given test subject 112 (e.g. one region for those test subjects likely to have a particular disease state and one region for those that are unlikely to have the disease state). The control group dataset thus contains as many homogeneous groups of individuals as necessary for the classification problem. Each individual in the control group is assigned a state of nature $\omega$. For example, two states of nature may be defined in the system: $\omega_1$ or normal subjects and $\omega_2$ for patients. Each control subject vector 804 is projected into the classification eigenspace C*.

In the intensity data and spatial data calculation steps S206, S208 discussed previously, a set of vectors are created that represent particular features of the VOI of a given control subject. The vector representing a particular feature for each control group subject i, belonging to state $\omega$, is projected into the corresponding restricted Allowable Domain for that feature. For example, if each control subject i has a control subject trace vector (t) 612 and a control subject intensity vector (g) 512, then vector (t) 612 of each subject i belonging to state $\omega$ is projected into Domain T* forming eigencoordinate vector $\tau_i$. Similarly, vector (g) 512 is projected into Domain G* forming eigencoordinate vector $\gamma_i$.

A number of possible features may be calculated on the distribution of eigencoordinate vectors. One possibility is to use the eigenposition along the principal component axis. If the distribution of the eigencoordinate vectors is assumed to be normal (Gaussian) then the formulation of feature vectors c for each subject i within classification eigenspace C* may be represented as:

$$c_i^\omega = \gamma_i^\omega \cup \tau_i^\omega$$

where $\omega$ indicates which state the control subject belongs to.

Based on the control group subject data 804, a multivariate linear discriminant analysis (LDA) classifier is built in the classification eigenspace C*, in step S806. Linear discriminant functions 808 are defined for this purpose. For example, if there are two states $\omega_1$ and $\omega_2$, the following discriminant function f(c) 808 might be built:

$$f(c) = w^d c + w_0$$

where w is the weight vector, d represents the dimension of classification eigenspace C*, c is the feature vector of a subject expressed in eigencoordinates, and $w_o$ is the bias or threshold weight. The parameters into a given linear discriminant function 808 (weight vector and bias/threshold weight) determine the orientation and location of a linear decision boundary. These parameters are based on the control group subject data 804. For example, these parameters may be set automatically using statistics software such as SYSTAT, JMP IN or MATLAB.

For a two-state classifier, the classification rule for linear discriminant function 808 may be stated as:

decide $\omega_1$ if $f(c) > 0$ and $\omega_2$ if $f(c) \leq 0$

Though not necessary to the present invention, in an effort to further reduce the dimensionality of the classification eigenspace C*, it is possible to select only the most significant eigenvectors for classification in C*, based on the control group subject data 804. This might be done in a multi-level fashion, by selecting the most significant eigenvectors in each Allowable Domain separately (e.g. T* and G*). These spaces would be combined to form a new classification eigenspace of reduced dimensionality. Forward stepwise regression, backward stepwise regression and Wilks' lambda statistics are among the numerous methods that may be used in the determination of significant eigenvectors in this process.

Figure 9:
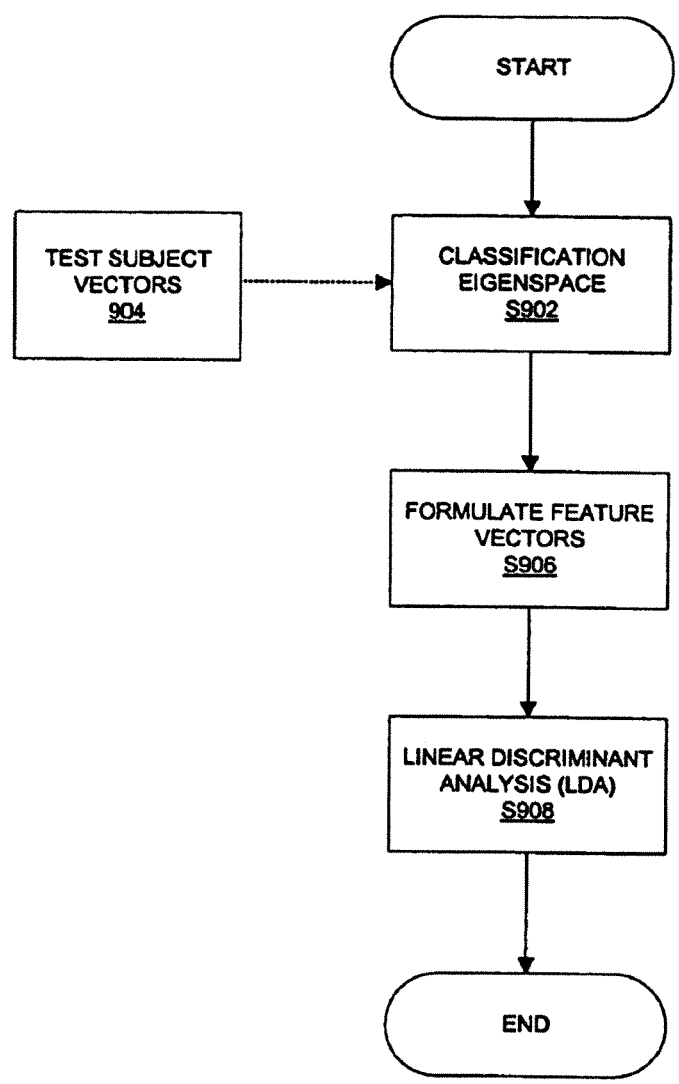

The classification of a new test patient 112 in step S214 is more particularly illustrated in FIG. 9. In the intensity data and spatial data calculation steps S206, S208 discussed previously, a set of vectors are created that represent particular features of the VOI of a given test subject. The vector representing a particular feature for the test subject 112 is projected into the classification eigenspace C* in step S902 in the same manner as described above for the control group subject data 804 to formulate a feature vector for that subject in step S906. The resulting feature vector is then analyzed according to LDA discriminant functions 808 built in the classification building step S212. Other types of classifiers that might be employed include logistic regression, artificial neural networks and support vector machines.

The automated classification system 102 has been successfully applied to temporal lobe epilepsy (TLE) lateralization, as described in S. Duchesne, N. Bernasconi, A. Bernasconi, D. L. Collins, "Temporal lobe epilepsy lateralization based on MR image intensity and registration features", Conference Proceedings of MICCAI, Springer Verlag, (2003), 2879(1): 367-374, the contents of which are incorporated herein by reference. TLE is defined by seizures originating in the medial temporal lobe (MTL). Since the majority of TLE patients are resistant to anticonvulsant drugs but can be helped by surgery, the present invention is useful in the automated lateralization of the seizure focus as being left or right MTL in origin. Currently, lateralization is performed on the basis of volumetric analysis of hippocampal atrophy and requires a priori segmentation of the hippocampus.

In the data collection step S202, the population subjects 110 are selected. They consist of 150 reference subjects (taken from the International Consortium for Brain Mapping database), 150 training subjects (in this case, the same set of subjects as the reference subjects), and 138 control subjects (consisting of 51 normal subjects and 87 patients). The normal subjects in the control group are different from those in reference and model training group. The patients in the control group are further subdivided into groups of patients with left TLE (47) and right TLE (40) as determined by manual volumetry. 3D MRI brain images are gathered in step S304 for each subject using a 1.5 T scanner T1-fast field echo sequence.

Recent observations in patients with TLE, in N. Bernasconi, A. Bernasconi, Z. Caramanos, S. B. Antel, f. Andermann, and D. L. Arnold, "Mesial temporal damage in temporal lobe epilepsy: a volumetric MRI study of the hippocampus, amygdala and parahippocampal region", Brain, Vol. 126(Pt 2), February 2003, pp. 462-9, the contents of which are hereby incorporated by reference, indicate that the epileptogenic zone is broad. The research suggests that the substrate for seizure generation is distributed over a network of brain structures in the MTL and not just the hippocampus. Thus, in this application, a large non-specific VOI centred on the left MTL is selected in step S204, capturing the hippocampus and neighbouring structures. The VOI is 360800 voxels in size (55×82×80).

This application uses both intensity and trace vectors. The calculation of intensity data in step S206 consists of the voxel-by-voxel difference between a subject VOI image and the mean of all subject VOI images in the training group, resulting in the following subject intensity vector 512:

$$g = v_{subject} - v_{average}$$

The calculation of spatial data in step S208 consists of the trace of the Jacobian matrix of the deformation field for a given subject VOI image, which is an indicator of morphological change (namely, the local volume change at each voxel). This results in the following subject trace vector 612:

$$t = v_{subject} - v_{average}$$

where, $$v = v_{local\ volume\ change} \approx tr(\nabla U)$$

The creation of linear variation models 706 in step S210 is based on intensity and trace model subject training vectors 512, 612. The first 25 eigenvectors for each model (25 trace, 25 intensity) were chosen, for a total of 50 eigenvectors in the classification space.

Three states of nature are defined for the classifier building step S212. Normal subjects ($\omega_1$), left TLE ($\omega_2$), and right TLE ($\omega_3$). The prior probabilities for each state of nature are $p(\omega_1)$= 0.37, $p(\omega_2)$=0.34, and $p(\omega_3)$=0.29. The first classification performed distinguishes between normal ($\omega_1$) and TLE ($\omega_2$, $\omega_3$) states. A backward stepwise regression is used, which reduces the number of eigenvectors kept from 50 to 20. The second classification performs lateralization of the TLE. A forward stepwise regression with identical tolerance as previously used is employed.

To classify each test patient 112 in step S214, a feature vector is formulated in step S908 for each test subject 112:

$$p_i^\omega = \gamma_i^\omega \cup \tau_i^\omega$$

In this example, the results of classifying each subject in the control group as a test subject 112 are summarized below. Table 1 summarizes the results of the first classification between normal and patient subjects (accuracy 95%) and Table 2 summarizes the results of the TLE lateralization (accuracy 75%).

TABLE 1

True positive results on the Normals-Normals/TLE-TLE diagnonal, shown in bold

|  | Normals | TLE | % correct |
|---|---|---|---|
| Normals | 45 | 6 | 88 |
| TLE | 1 | 86 | 99 |
| Total | 46 | 92 | 95 |

TABLE 2

True positive results on the Left-Left/Right-Right diagonal, shown in bold

|  | Left | Right | % correct |
|---|---|---|---|
| Left | 36 | 11 | 77 |
| Right | 11 | 29 | 73 |
| Total | 47 | 40 | 75 |

Another example of the successful application of the automated classification system 102 is its application to the successful computerized differentiation of Alzheimer's dementia (AD) and mild cognitive impairment (MCI) from normal aging (NA). AD is a progressive neurodegenerative disorder. Currently, the diagnosis of clinically probable AD can be made with high accuracy in living subjects only once the stage of dementia has been reached, and requires clinical, neuropsychological and imaging assessments. Early detection of AD is therefore critical if treatment is to be effective.

In the data collection step S202, the population subjects 110 are selected. They consist of 152 reference subjects, 152 training subjects, and 44 control subjects (consisting of 22 normal subjects, 15 subjects with AD, and 7 subjects with MCI). 3D MRI brain images are gathered in step S304 for each subject with T1-weighted MRI protocol on a 1.5 T scanner using a fast gradient echo sequence.

Neuropathological studies, such as in J. R. Petrella REC, P. M. Doraiswamy, "Neuroimaging and Early Diagnosis of Alzheimer Disease: A Look to the Future", Radiology 2003, 226(2):315-336, the contents of which are incorporated herein by reference, have shown that brain degeneration occurs very early in the course of the disease, even before the first clinical signs, in certain regions such as the medial temporal lobe (MTL). In this application, a large non-specific VOI centered on the left MTL is selected in step S204. The VOI is 55×82×80=360800 voxels in size and captures the hippocampus and neighboring MTL structures, such as the parahippocampal gyrus.

Both intensity and trace vectors are employed in this application. Intensity data is calculated in step S206 by taking the voxel-by-voxel difference between a subject VOI image and the mean of all subject VOI images in the training group, resulting in the following subject intensity vector 512:

$$g = v_{subject} - v_{average}$$

The calculation of spatial data in step S208 consists of the trace of the Jacobian matrix of the deformation field for a given subject VOI image, which is an indicator of morphological change (namely, the local volume change at each voxel). This results in the following subject trace vector 612:

$$t = v_{subject} - v_{average}$$

where, $$v = v_{local\ volume\ change} \approx tr(\nabla U)$$

Linear variation models 706 are created in step S210 based on intensity and trace model subject training vectors 512, 612. The first 40 eigenvectors were chosen for the classification eigenspace.

Three states of nature are defined for the classifier building step S212, normal subjects ($\omega_1$), AD subjects ($\omega_2$), and MCI subjects ($\omega_3$). The prior probabilities for each state of nature are $p(\omega_1)$=0.50, $p(\omega_2)$=0.34, and $p(\omega_3)$=0.16. Forward stepwise regression was used to select eigenvectors that yielded maximal discrimination between the groups. The first classification distinguishes between normal ($\omega_1$) and AD ($\omega_2$) states, after reducing the number of eigenvectors from 35 to 3 with the stepwise process. The second classification distinguishes between normal ($\omega_1$) and AD+MCI ($\omega_2$, $\omega_3$) states, after reducing the number of eigenvectors from 40 to 2 with the regression model. The third classification distinguishes between AD ($\omega_2$) and MCI ($\omega_3$) states, after reducing the number of eigenvectors from 20 to 3 with the regression model.

Tables 3, 4 and 5 summarizes the results of the three classifications, respectively.

TABLE 3

True positive results on the AD-AD/Normal-Normal diagonal, shown in bold

|  | AD | Normal | % correct |
| --- | --- | --- | --- |
| AD | 15 | 0 | 100 |
| Normal | 0 | 22 | 100 |
| Total | 15 | 22 | 100 |

TABLE 4

True positive results on the AD + MCI-AD + MCI/Normal-Normal diagonal, shown in bold

|  | AD + MCI | Normal | % correct |
| --- | --- | --- | --- |
| AD + MCI | 22 | 0 | 100 |
| Normal | 0 | 22 | 100 |
| Total | 22 | 22 | 100 |

TABLE 5

True positive results on the AD-AD/MCI-MCI diagonal, shown in bold

|  | AD | MCI | % correct |
| --- | --- | --- | --- |
| AD | 12 | 3 | 80 |
| MCI | 0 | 7 | 100 |
| Total | 12 | 10 | 90 |

These examples serve to illustrate the potential applicability of the present automated classification system to the detection of neurological diseases or disorders. Schizophrenia is another example of a neurological disorder that the present invention may be applied to. The system might also be applied as a differentiator between Alzheimer's dementia and other types of dementia such as frontal lobe dementia, Parkinson dementia, and vascular dementia. Studies on movement disorders may also be conducted using the present invention.

Having described aspects of the prior art, embodiments of the present invention will now be described.

Figure 10:
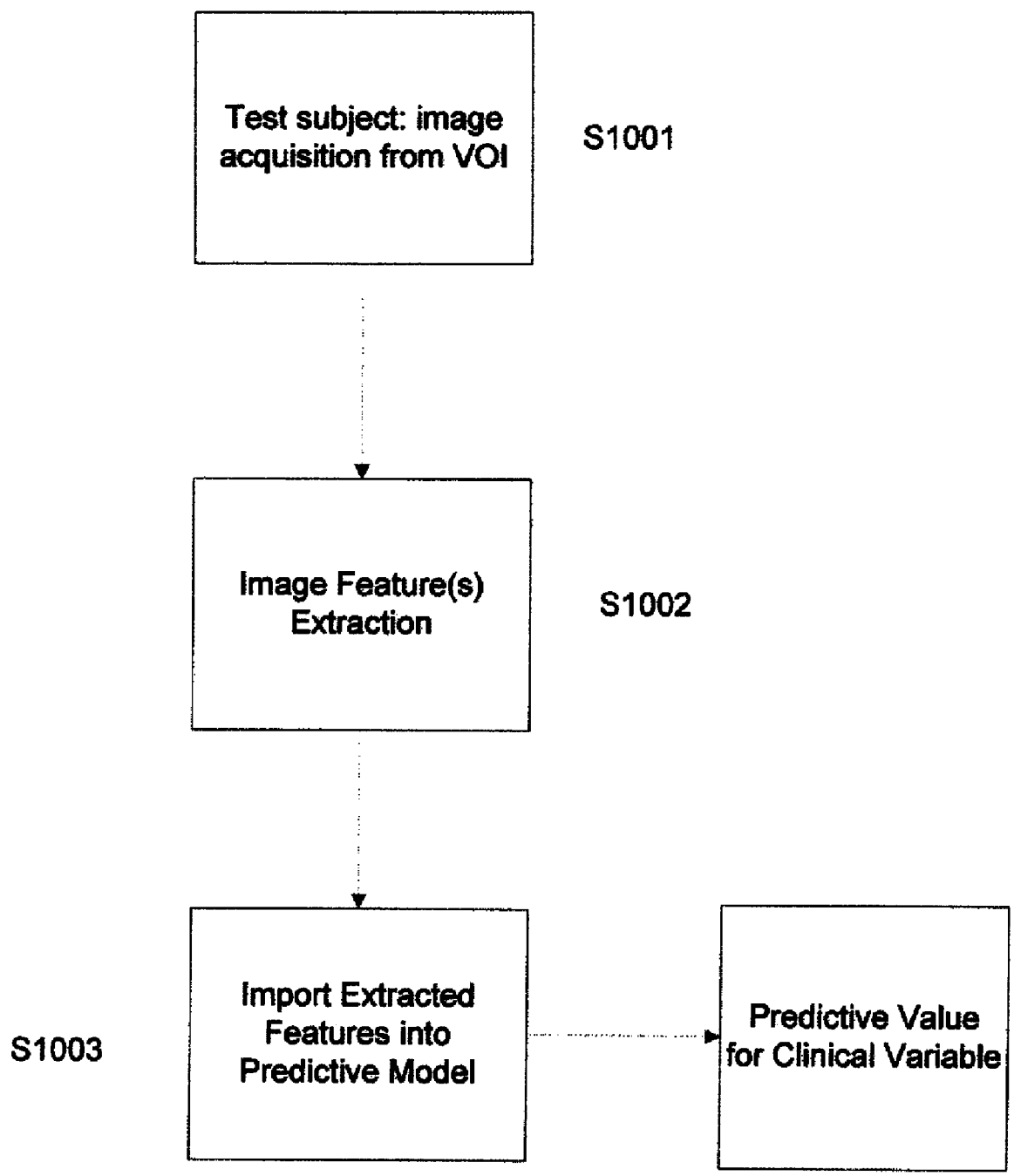
FIG. 10 is a flow chart illustrating exemplary steps for predicting a clinical state of a subject.

In one aspect of the invention there is provided a method for predicting the evolution of the state of a subject. By state of a subject it is meant a clinical state which relates to the physiological or health state of the subject. Preferably the state of the subject refers to the physiological or health state of a particular organ or system of the subject. For example, the method can be used to predict the evolution of the state of a subject with regard to his or her cardiac system, nervous system and the like. The method is generally illustrated in FIG. 10 wherein image-based data from a subject is imported into a predictive model to obtain a predictive value for the future state of the subject. Thus, one or more images are acquired at step S1001 from a volume of interest (VOI) of a subject and at least one image feature is extracted or measured, step S1002 and imported in the predictive model, step S1003 to generate a predictive value of the evolution of a state of the subject. The state of the subject may be assessed by known clinical scales. These clinical scales are well known in the art and are function of the state to be assessed. A few examples of clinical scales include but are not limited to MMSE for assessing MCI, tumor staging for assessing the aggressiveness of a cancer and the like.

The predictive model is a statistical image-based model that is established by providing a correlation function between one or more image features and a future value of a clinical variable that represents a measure on a given clinical scale. The establishment of the model is realized by acquiring data from a group of training subjects.

As mentioned previously, the image data can be acquired using any imaging modality suitable for acquiring information from a given volume of interest (VOI). Such modalities include but are not limited to MRI, including structural, spectroscopic, functional, diffusion, and magnetization transfer MRI, near infrared imaging, optical imaging, microwave imaging, X-ray, ultrasound, PET, SPECT, CT, scintigraphy, tomosynthesis, fluoroscopy, portal imaging, and combinations thereof. The model may incorporate variables from more than one imaging modality.

The selection of the training subjects is in part dictated by the particular clinical state for which the establishment of a predictive model is desired. Thus the training subjects may include subjects that have been assessed as presenting characteristics of a given clinical state. Thus, in one embodiment of the invention images of one or more VOIs of the subjects are acquired and the subjects are then clinically assessed over time using an appropriate clinical scale for the state for which a prediction is desired. The model is built based on a univariate or multivariate analysis of one or more image features and one or more clinical variable.

It will be appreciated that the model may incorporate image features representative of various stages of evolution of a particular state. Thus, the model can be built based on images acquired over a period of time for each training subject. In another alternative embodiment the images from subjects that are at different stages of a given clinical stage may be acquired. For example if the evolution of a particular state, say a neurodegenerative disorder, is age dependent the training group can include subjects of different ages.

The image features that are derived from the images in order to build the model and to obtain a predictive value for the evolution of a state of subject can be any features commonly known in the art to be extractable from the image. As described above, the features can be classified in two broad categories. One related to the image signal and the other to the spatial-shape characteristics. By image signal it is meant the information encoded at each voxel of the image data such as the intensity of the signal. Other type of information can be encoded in the voxel such as the lifetime of the signal, information about its frequency (such as the wavelength of light in optical imaging) and the like. By spatial-shape characteristics it is meant morphologic information about the VOI. For example, the spatial-shape characteristics of a VOI may represent anatomical structure within the VOI. Image features from any combination of voxels or all voxels within a VOI can be used in a model. Image features are also meant to include any information that is convey by a particular dimensionality of the image. People skilled the art will recognize that information provided by an imaging modality can be expressed in single or multi-dimensional spaces.

Figure 11:
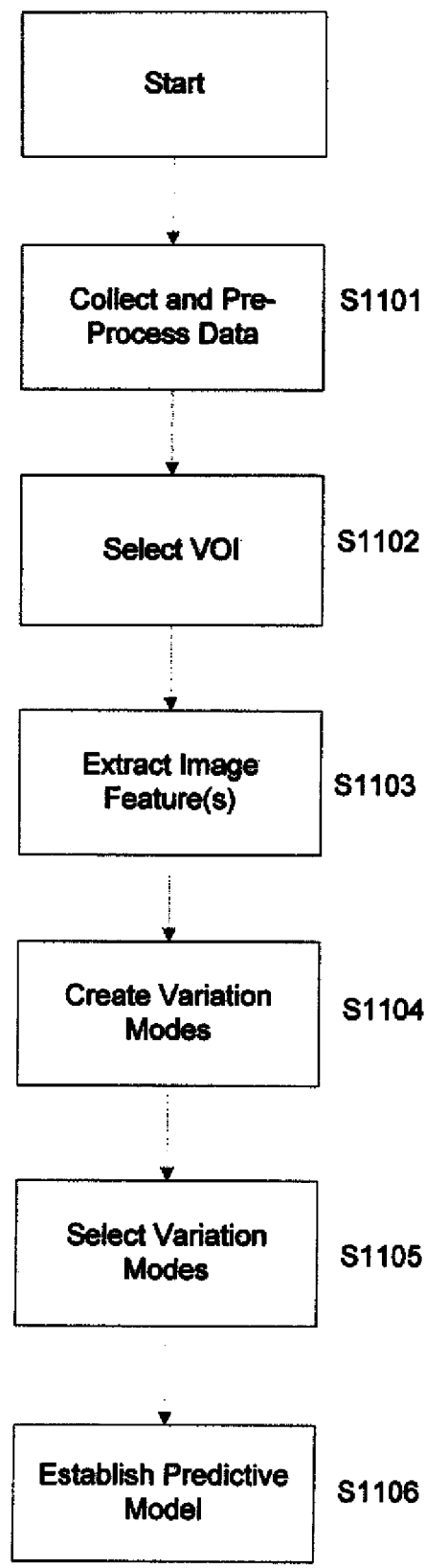
FIG. 11 is a flow chart further illustrating exemplary steps for predicting a clinical state of a subject.

The model can be built by deriving a set of modes of variation of image features from a plurality of training subjects and selecting a subset of the modes of variation based on univariate or multivariate analysis, or a combination of both, between the modes of variation and at least one clinical variable. The selected subset is then used to provide a relationship, based on univariate or multivariate analysis, or a combination of both between one or more image features of a test subject and one or more clinical variable. In one embodiment the modes of variations can be derived as described above. With reference to FIG. 11 the establishment of the predictive model comprises: collecting image data from training subjects at step S1101, selecting one or more VOIs at step S1102, extracting one or more image features at step S1103, creating variation modes at step S1104, selecting variation modes at step S1105 and establishing the predictive model at step S1106.

The model may also comprise variables other than image features. For example the model may comprise demographic information (age, sex, etc.) or results from a clinical test or any other variable that can increase the accuracy of the model.

It will also be appreciated that the predictive model may be generated based on en ensemble of training subjects that have been classified as described above. Thus while it is possible to use a clinical scale to assess the training subjects at different points in the evolution of the clinical state, it is also possible to classify the training subjects using the classification method as described in FIGS. 1-9.

The predictive ability of the model can be assessed using appropriate statistical analysis based on the predicted and actual values. For example, the predictive ability can be assessed by computing F-statistics based on the residuals of predicted vs actual values for the clinical variable.

In another aspect of the invention, the predictive model can be used in a patient management program for establishing a treatment protocol based on a predicted evolution of a state of a subject. The predictive model can be also be used for selecting subjects in a clinical trial or study to improve the development more reliable epidemiological protocols.

In yet another aspect of the invention there is also provided a system for predicting an evolution of a state of a subject, comprising one or more imaging devices for acquiring imaging data, an image processor for providing image features measurements of at least one volume of interest (VOI) of the subject and a predictive model calculator for providing a predictive value of a state.

EXAMPLES

The following examples describes the establishment of a predictive model for Mild Cognitive Impairment but the person skilled in the art will appreciated that other disease states as well as normal states can also be predicted by an appropriately built predictive model. Disease states that can be predicted include but are not limited to temporal lobe epilepsy, general, focal, temporal lobe, frontal lobe_dementias alzheimer, parkinson, lewy bodies, vascular, fronto-temporal, multiple sclerosis including primary progressive, secondary progressive, relapse-remitting, mild cognitive impairment, epilepsies multiple systems atrophy, progressive supranuclear palsy, corticobasal degeneration.

Prediction of Mild Cognitive Impairment

MCI is widely viewed as the transition phase between normal aging and Alzheimer's disease (AD) and amnestic MCI individuals are known to be at risk for progression to AD. There is evidence that in those who will progress, measurable hippocampal and entorhinal cortex atrophy, demonstrable on T1w MRI serves as a moderate, though labor-intensive, predictor. Microscopically the strongest predictor of premortem cognitive dysfunction appears to be the relative area of entorhinal cortex occupied by beta-amyloid deposition. Existing MRI measures that have been developped to predict decline are longitudinal, as for example a study by Rusinek et al showing that an increased rate of atrophy in the MTL predicted future cognitive decline.

The Ethics Committee of the Montreal Neurological Institute (Montreal, Canada) and the IRCCS San Giovanni di Dio FBF (Brescia, Italy) approved the study and informed consent was obtained from all participants. A total of 199 subjects were included in this study. The reference group consisted in 152 young, neurologically healthy individuals from the International Consortium for Brain Mapping database (ICBM) whose scans were used to create the non-pathological, reference space. The training population consisted in 47 MCI patients ($23 \leq$ MMSE$<30$), seen at the IRCCS San Giovanni di Dio FBF Hospital, that have been followed clinically a minimum of 12 months after their initial MR scan.

MRI data for our 152 ICBM subjects was collected with a T1w MRI protocol on a 1.5 T scanner (Philips Gyroscan, Best, Netherlands) using a fast gradient echo sequence (TR=18 ms, TE=10 ms, 1 NEX pulse sequence, flip angle=30°, matrix size=256×256, FOV=256 mm, slice thickness=1 mm). Data for MCI patients were acquired on a 1.0 T scanner (Philips Gyroscan, Best, Netherlands) using an FFE sequence (TR=19.7 ms, TE=6.9 ms, sagittal acquisition, 0.9365×0.9375×1.3 mm$^3$). All global MRI data were processed to correct for intensity non-uniformity due to scanner variations. The 152 ICBM subjects were registered in a Talairach-like stereotaxic space in the context of the ICBM project. Most (33/47) of the MCI data were linearly registered (9 DoF) automatically into stereotaxic space while the remaining volumes were manually registered due to high scalp brightness. All reference and training volumes were resampled onto a 1 mm isotropic grid.

Two VOIs were selected for this study, centered on the left and right medial temporal lobe, using Talairach coordinates (start coordinates x=[−57,+2] for the left and right side respectively, y=−53 and z=−52). Each VOI measured n=55×82×80=360800 voxels. The VOI was selected so that its extent captured the hippocampus and neighboring MTL structures (e.g. ento and perirhinal cortex, parahippocampal gyrus), irrespective of normal inter- and intra-individual variability. After extraction, each VOI was linearly registered (9 DoF) to the reference volume to further reduce local distortions, and its mean intensity scaled to the mean intensity of the reference VOI, which serves to eliminate the first-order drift in signal measurement between patients.

Two image features at each voxel location were retained. The first feature is the grey level intensity consisting in the rasterized data from the intensity-scaled VOIs. The second feature is the trace or the first-order approximation of the determinant of the Jacobian matrix of a non-linear registration-derived deformation field. The latter is calculated to map each subject's VOI to our reference ICBM target. The trace represents an estimate of local volume change. Principal Components Analysis (PCA) is used to reduce the dimensionality of the input training data and generate linear variation models based on the N=152 datasets from our ICBM normal subjects. The resulting four PC models were each p=N-1 (or 151-dimensional). Most of the variation can usually be explained by a smaller number of modes, I, where I<<n and I<p. We proceeded in selecting 535 eigenvectors in total from our four models (left/right intensity/trace VOs),that accounted to a per-model variance of 99.7%.

The predictive model may be obtained as follows: an eigenspace from a large training group of subjects is generated as described above. Then test subjects image data are projected in the reference eigenspace to calculate a correlation coefficient between the projection coordinates and the clinical variable for each eigenvector. Thus rasterized vectors of the processed VOI image features for each test subject are projected into the training space, and thus form eigencoordinate vectors. For each eigenvector the correlation of the eigencoordinate distribution with the clinical variable is then computed. A pre-determined threshold for the correlation coefficient is selected and used to identify eigenvectors for the predictive model. Finally, a predictive model is then built from those eigenvectors using multiple regression (for example: JMP IN, SAS Institute, Cary, N.C.). The model is then used to predict the future value of the clinical variable of interest.

A number of possible features can be calculated on the distribution of the projected data. One example is to take a predictor that is based on the position along the PC axes. The distribution of eigencoordinates along any principal component for a given population is normally distributed as assessed via Shapiro-Wilke statistics.

The selection of the q eigenvectors for the predictive model was based on an arbitrarily predefined threshold for the correlation coefficient of $r>|0.30|$.

Four experiments were completed. Experiment 1 served as a baseline for the classification of our patient population into 3 groups based on their MMSE changes at 1 year follow-up from clinical variables (age, sex, baseline MMSE). Experiment 2 attempted the same 3-group classification but this time based on the projection eigencoordinates in the reference space. Experiment 3 served as a baseline for the prediction of yearly MMSE decline by building a linear model based on clinical variables ("Clinical"). Experiment 4 attempted the same prediction but with a model based on projected eigencoordinates, as per the methodology described above ("MRI"), while in Experiment 5 we added baseline MMSE as an additional variable to the projected eigencoordinates ("MRI+baseline MMSE").

Results

When comparing MMSE results between baseline and 12 months follow-up, we can separate the 47 patients in the test population into three distinct groups: 16 decliners (>−1 point negative change in MMSE or cognitive decline), 5 improvers (>1 point positive change in MMSE or cognitive improvement), and 26 stable individuals (MMSE change between [−1,1]). Demographic information about each group can be found in FIG. 12 There was no statistically significant age difference between either groups, as assessed from ANOVA and Tukey-Kramer HSD P>0.05, DF=2). There was a statistically significant baseline MMSE difference between the decliners and improvers (P=0.0003, DF=2), but no other significant difference between groups for baseline MMSE. The improvers had the lowest mean baseline MMSE of all three groups.

Figure 12:
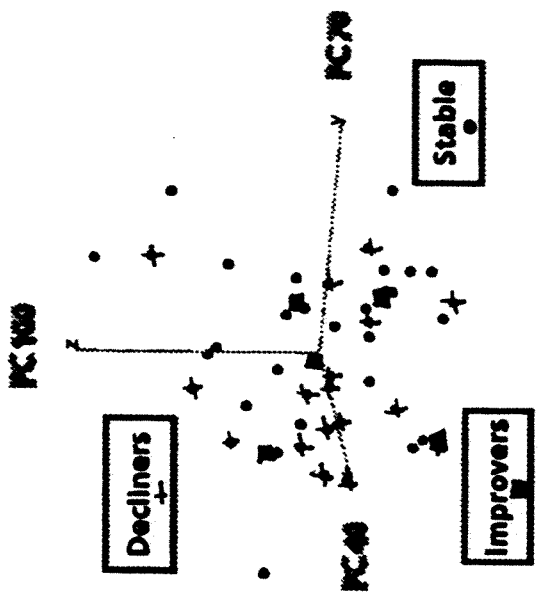
FIG. 12 A Demographic information. B Leave-one-out, forward stepwise linear discriminant analysis of the patient eigencoordinates in the reference space was 100% accurate at classifying groups (decliners, stable, improvers). The data is shown here projected on the 3 most discriminating eigenvectors.

The classification was based on a leave-one-out, forward stepwise linear discriminant analyses (SYSTAT 10.2, Georgia, Pa.; P-to-enter<0.05) of either clinical variables (age, sex and baseline MMSE) or eigencoordinates along the 535 reference space eigenvectors. The clinical classifier of Experiment 1} was 53% accurate in separating the 47 patients into decliners, improvers and stable subjects (DF=2, Wilk's \lambda=0.69), while the 3-way classifier based on projection eigencoordinates of Experiment 2 was 100\% accurate, with 31 significantly discriminant eigenvectors (P-to-enter<0.05 , DF=31, Wilk's \lambda=0). FIG. 12 displays the data plotted along the three most discriminating eigenvectors.

TABLE 6

| Model | Features | r | $r^2$ | SD | F stat To Clin. | P | F Stat to MRI | P |
|---|---|---|---|---|---|---|---|---|
| Clinical | 3 | 0.429 | 0.176 | 1.86 | — | — | — | — |
| MRI | 10 | 0.668 | 0.446 | 1.53 | 2.499 | 0.003 | — | — |
| MRI + MMSE | 11 | 0.696 | 0.484 | 1.48 | 2.691 | 0.002 | 2.585 | 0.002 |

Figure 13:
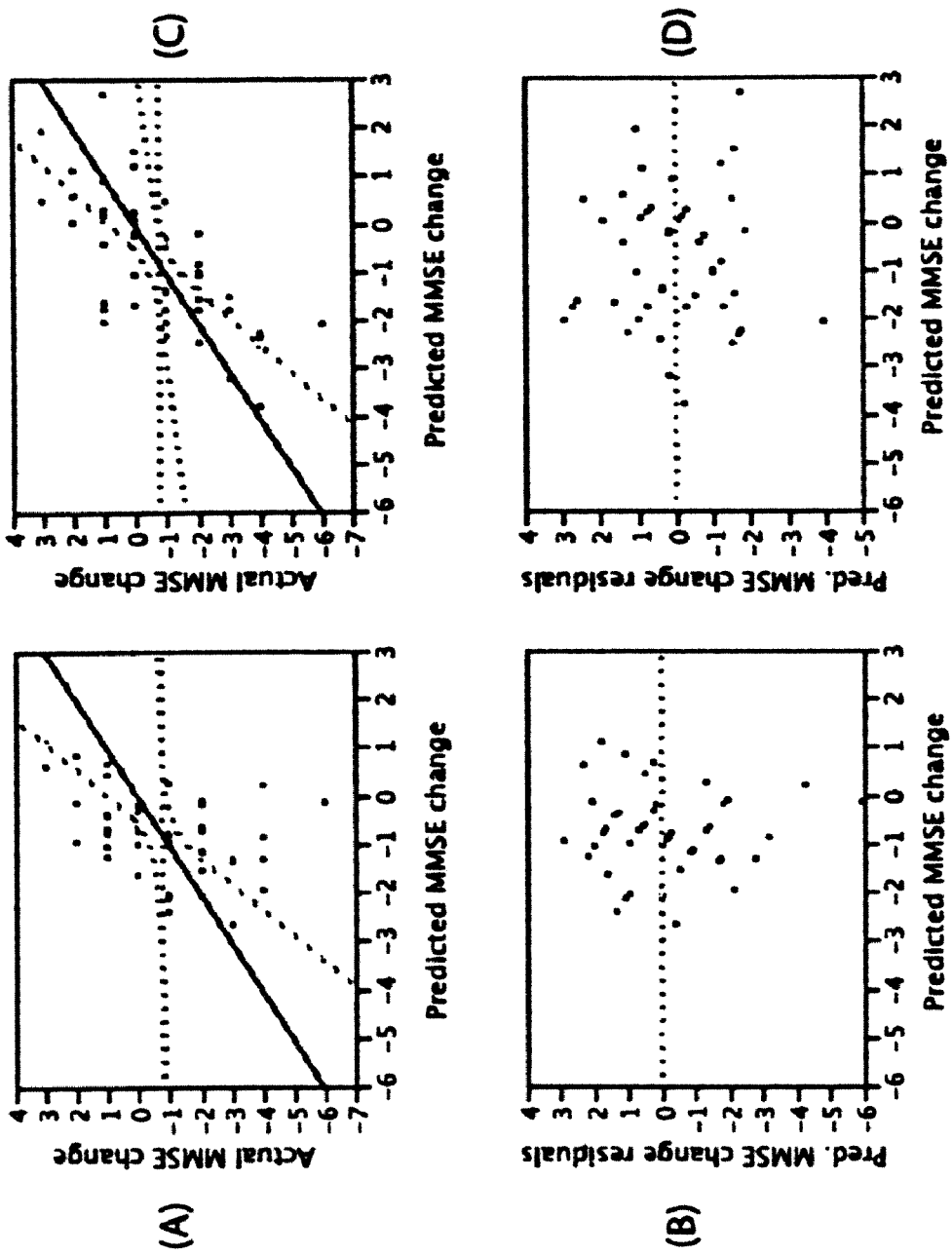
FIG. 13 (A) Clinical model built from multiple regression of age, sex and baseline MMSE against 1 year MMSE changes. (B) Residuals for the "Clinical" model. The correlation of predicted vs actual values was r=0.429. (C) MRI+ Baseline MMSE model built from multiple regression of the 10 most correlated reference space eigenvectors plus baseline MMSE. (D) Plot of residuals. With a correlation between predicted vs actual yearly MMSE changes of r=0.6955, this model was a significant improvement over the "Clinical" one (F-stat=2.691, P=0.002).

Experiments 1 and 2 classified the data into groups. In the following 3 experiments the magnitude of the yearly MMSE change is predicted. Baseline MMSE, age and sex were all negatively and weakly correlated with 1 year MMSE change (r=−0.25, r=−0.21 and r=0.15, respectively). In contrast, out of the 535 reference space eigenvectors, 10 had a correlation ratio of r>|0.30|. We predicted MMSE change for all patients using each linear model. The number of input features to the model, the resulting correlation (r) and squared correlation ($r^2$) of predicted vs. actual values, the standard deviation of the predicted score and F-test values (against "Clinical" and "ICBM") are shown in table 6. Recall that the first predictive model (Experiment 3) is based on the 3 clinical variables ("Clinical"), the second (Experiment 4) on the 10 selected eigenvectors ("MRI") and the last (Experiment 5) using the 10 eigenvectors plus the baseline MMSE ("MRI+baseline MMSE"). The linear fit for the "Clinical" and "MRI+baseline MMSE" models are shown in FIG. 13 alongside their residual plots. The best model was the "MRI+baselineMMSE" of Experiment 5, with a correlation between predicted and actual value of r=0.6955. It was also significantly better than either the "Clinical" model (Fstat=3.39, P=0.0001, DF1=43, DF2=35) or the "MRI" model (Fstat=2.59, P=0.002, DF1=36, DF2=35).

The aforementioned and other features, benefits and advantages of the present invention can be understood from this description and the drawings by those skilled in the art. The above described exemplary embodiments of this invention are intended to be illustrative and in no way limiting. Many modifications are possible in the exemplary embodiments without materially departing from the novel teachings and advantages of this invention. All such modifications are intended to be encompassed within the scope of the present invention, as defined by the claims.

The invention claimed is:

1. A method for predicting an evolution of a clinical state of a subject, comprising:
   determining a present state on a clinical scale, said clinical scale representing various stages of clinical evolution of a clinical state;
   providing in a computer a statistical image-based predictive model for predicting said evolution of said clinical state, said model incorporating one or more image-derived features derived from an image from at least one volume of interest (VOI) comprising information related to said clinical state, wherein
      said statistical image-based model is established by providing a correlation function between one or more image features and a future value of a clinical variable that represents a measure on said clinical scale, and
      establishment of said statistical image-based model is realized by acquiring data from a group of training subjects;
   collecting image data from said at least one VOI in said subject;
   deriving in a computer said one or more image features from said collected image data from said subject;
   using in a computer said one or more derived image features from said at least one VOI of said subject and said predictive model to generate said measure on said clinical scale, wherein
      said measure is indicative of a future state on said clinical scale providing at least an indication of improvement, stability or degradation of said clinical state with respect to said present state.

2. The method as claimed in claim 1 wherein said image data are collected using one or more imaging modalities selected from the group consisting of MRI, including structural, spectroscopic, functional, diffusion, and magnetization transfer MRI, near infrared, optical imaging, microwave imaging, X-ray, ultrasound, PET, SPECT, CT, scintigraphy, tomosynthesis, fluoroscopy, portal imaging, and combinations thereof.

3. The method as claimed in claim 2 wherein said one or more image features are selected from image signal, spatial shape characteristics and combinations thereof.

4. The method as claimed in claim 3 wherein said image signal and said spatial shape characteristics are derived from all voxels in said VOI or any combination of voxels from said VOI.

5. A method for predicting an evolution of a clinical state of a subject, comprising:
   determining a present state on a clinical scale, said clinical scale representing various stages of clinical evolution of a clinical state;
   providing in a computer a statistical image-based predictive model for predicting said evolution of said clinical state, said model incorporating one or more image-derived features derived from an image from at least one volume of interest (VOI) comprising information related to said clinical state;
   collecting image data from said at least one VOI in said subject;
   deriving in a computer said one or more image features from said collected image data from said subject;
   using in a computer said one or more derived image features from said at least one VOI of said subject and said predictive model to predict a future state on said clinical scale providing at least an indication of improvement, stability or degradation of said clinical state with respect to said present state, wherein said statistical image-based predictive model is generated by:
      deriving a set of modes of variation of said image features from a plurality of training subjects;
      selecting a subset of said modes of variation based on a first univariate or multivariate analysis or combination thereof between said modes of variation and at least one clinical variable; and
      establishing said model based on a second univariate, or multivariate analysis or combination thereof between said selected subset of modes and said at least one clinical variable.

6. The method as claimed in claim 5 wherein said first univariate or multivariate analysis is used to produce a similarity coefficient and wherein said selection is based on a comparison of said correlation coefficient and a predetermined correlation coefficient.

7. The method as claimed in claim 5 wherein said second univariate or multivariate analysis is a multivariate regression.

8. The method as claimed in claim 5 wherein said clinical state is indicative of an evolution of a disease.

9. The method as claimed in claim 8 wherein said disease state is selected from mental health disorders, cardiac, musculo-skeletal, and cancer.

10. The method as claimed in claim 5 wherein image data from said plurality of training subjects are obtained from subjects at different stages of evolution of said clinical state.

11. The method as claimed in claim 5 wherein image data from said plurality of training subjects are obtained from subjects at similar stages of evolution of said clinical state.

12. The method as claimed in claim 5 wherein the age of said training subjects are different.

13. The method as claimed in claim 5 wherein image data from said plurality of training subjects are obtained over a period of time to generate a plurality of images for each training subject.

14. The method as claimed in claim 1 wherein said statistical image-based predictive model also incorporates at least one variable other than image features.

15. The method as claimed in claim 14 wherein said at least one other variable is from a clinical scale for a particular state.

16. The method as claimed in claim 5 wherein said image is a Magnetic Resonance Image (MRI).

17. The method as claimed in claim 16 wherein said one or more image features comprise an image signal.

18. The method as claimed in claim 17 wherein said image signal is a T1 weighted MR signal.

19. The method as claimed in claim 18 wherein said one or more image features comprise a spatial shape measurement.

20. The method as claimed in claim 19 wherein said spatial shape measurement is a volume change in said at least one VOI in a subject or training subject relative to an average volume.

21. The method as claimed in claim 19 wherein said state is a neurological disease state selected from the group comprising temporal lobe epilepsy, general, focal, temporal lobe, frontal lobe dementias alzheimer, parkinson, lewy bodies, vascular, fronto-temporal, multiple sclerosis including primary progressive, secondary progressive, relapse-remitting, mild cognitive impairment, epilepsies multiple systems atrophy, progressive supranuclear palsy, corticobasal degeneration and said at least one VOI is a brain VOI.

22. The method as claimed in claim 21 wherein said neurological disease is mild cognitive impairment and imaging data are collected from left and right medial temporal lobe thereby defining two VOIs.

23. The method as claimed in claim 22 wherein said clinical variable is a score of Mini-Mental State Examination.

24. The method as claimed in claim 21 wherein the at least one VOI comprises more than one brain structure.

25. The method as claimed in claim 5 wherein said modes of variation are obtained using Principal Component Analysis (PCA).

26. A method for patient management comprising predicting an evolution of a clinical state in a subject using the method of claim 1 and recommending a treatment protocol based on said prediction.

27. A method for selecting subjects in a clinical trial or study, comprising predicting an evolution of a clinical state in a group of subjects using the method of claim 1 to generate of predictive value for said clinical state and selecting subjects for study or trial based on said predictive value.

28. A system for predicting an evolution on a clinical scale representing various stages of clinical evolution of a clinical state of a subject, comprising one or more imaging devices for acquiring imaging data, an image processor for providing image features measurements of at least one volume of interest (VOI) of the subject and a predictive model calculator for providing a predictive value of said state, wherein said predictive model calculator uses a correlation function between one or more image features and a future value of a clinical variable that represents a measure on said clinical scale, said measure being indicative of a future state on said clinical scale providing at least an indication of improvement, stability or degradation of said clinical state with respect to a present state on said clinical scale.

29. A method for predicting the evolution of a clinical state of a subject, the method comprising:
    determining a present clinical state;
    importing image-based data indicative of the present clinical state of the subject into a predictive model, wherein the predictive model is a statistical image-based model;
    establishing a predictive value indicative of a future state of the subject from the predictive model; and
    predicting the evolution of the clinical state from the predictive value, wherein the evolution of the clinical state is indicative of at least one of improvement, stability or degradation with respect to the present clinical state.

30. The method as claimed in claim 29, wherein the clinical state is a mental health state, and said image-based data is brain scan data.

31. A method for predicting the evolution of a clinical state of a subject, the method comprising:
    selecting a group of training subjects according to the clinical state for which the establishment of the predictive model is desired;
    acquiring at least one image-based data from each training subject of the group of training subjects wherein, the at least one image-based data represents a volume of interest with respect to the clinical state;
    determining a clinical diagnosis for each training subject of the group of training subjects,
    wherein the clinical diagnosis is established at a future point in time with respect to the acquisition of the at least one image-based data;
    extracting at least one image feature from the at least one image-based data;
    providing a correlation function between the at least one image feature and the clinical diagnosis for each respective training subject; and
    establishing the predictive model according to the correlation function;
    determining a present clinical state of the subject;
    importing image-based data indicative of the present clinical state of the subject into the predictive model;
    establishing a predictive value indicative of a future state of the subject from the predictive model; and
    predicting the evolution of the clinical state from the predictive value, wherein the evolution of the clinical state is indicative of at least one of improvement, stability or degradation with respect to the present clinical state.

32. The method as claimed in claim 31, wherein the clinical state is mental health state, and said image-based data is brain scan data.

* * * * *